United States Patent [19]

Lee

[11] Patent Number: 5,059,611
[45] Date of Patent: Oct. 22, 1991

[54] ANTI-INFLAMMATORY 5-HYDROXY-2-FURANONES

[75] Inventor: Gary C. M. Lee, Laguna Hills, Calif.

[73] Assignee: Allergan, Inc., Irvine, Calif.

[21] Appl. No.: 427,268

[22] Filed: Oct. 25, 1989

Related U.S. Application Data

[63] Continuation-in-part of Ser. No. 273,300, Nov. 18, 1988, abandoned.

[51] Int. Cl.$^5$ ............... A61K 31/44; A61K 31/34; C07D 307/28
[52] U.S. Cl. ................... 514/336; 514/471; 514/473; 549/295; 549/313; 549/318; 549/320; 549/321; 549/218; 546/283
[58] Field of Search ............... 549/295, 321, 320, 218, 549/313; 514/473, 471, 336; 546/283

[56] References Cited

U.S. PATENT DOCUMENTS

| | | | |
|---|---|---|---|
| 2,359,096 | 9/1944 | Elderfield | 260/239.5 |
| 2,359,208 | 9/1944 | Elderfield | 260/344 |
| 4,447,455 | 5/1984 | Jacobs | 424/279 |
| 4,786,651 | 11/1988 | Wheeler | 514/460 |
| 4,789,749 | 12/1988 | Jacobs et al. | 549/313 |
| 4,855,320 | 8/1989 | Chatterjee et al. | 514/473 |

FOREIGN PATENT DOCUMENTS

| | | |
|---|---|---|
| 133376 | 2/1985 | European Pat. Off. |
| 209274 | 1/1987 | European Pat. Off. |
| 295056 | 6/1987 | European Pat. Off. |

OTHER PUBLICATIONS

Tocanne et al., "Absolute Configuration of Optically Active Paraconic Acid", CA 69 76581k (1968).
Bonjouklian et al., Chemical Abstracts, vol. 106, 156260c, p. 670 (1987).
Graziano et al., Chemical Abstracts, 107 (1987), 236559t.
Reynolds et al., J. Am. Chem. Soc., 110, pp. 5172–5177 (1988).
Deems et al., Biochimica et Biophysica Acta, 917, pp. 258–268 (1987).
Scheuer et al., Journal of the American Chemical Society, 100:1, p. 307 (Jan. 4, 1978).
Roll et al., Org. Chem., 1988, 53, 3276-8.
Negishi et al., J. Org. Chem., 45, pp. 5223–5225 (1980).
Nakagawa et al., "Aldose Reductase Inhibitor from Palaun Sponges", Chem. Abstract, 106:96126b.

*Primary Examiner*—C. Warren Ivy
*Assistant Examiner*—Amelia A. Owens
*Attorney, Agent, or Firm*—Martin A. Voet; Gabor L. Szekeres; Howard J. Klein

[57] ABSTRACT

New 5-hydroxy-2-furanone compounds have anti-inflammatory, immunosuppressive and anti-proliferative activity and are useful in treating psoriasis and modifying calcium homeostasis.

11 Claims, No Drawings

ANTI-INFLAMMATORY 5-HYDROXY-2-FURANONES

CROSS-REFERENCE TO RELATED APPLICATION

This application is a continuation-in-part of application Ser. No. 273,300 filed on Nov. 18, 1988, now abandoned.

This invention relates to new 5-hydroxy-2-furanone compounds having anti-inflammatory activity, pharmaceutical compositions comprising these compounds and to methods of using them.

BACKGROUND OF THE INVENTION

Manoalide is a furanone compound isolated from marine sponge as reported by E. D. de Silva et al., Tetrahedron Letters 21:1611–1614 (1980). Anti-inflammatory, immunosuppressive and analgesic properties of manoalide are disclosed in U.S. Pat. No. 4,447,445. Manoalide has the following structural formula:

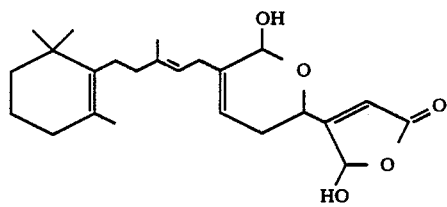

The anti-inflammatory activity of seco-manoalide and dehydro-seco-manoalide is also disclosed in U.S. Pat. No. 4,447,445.

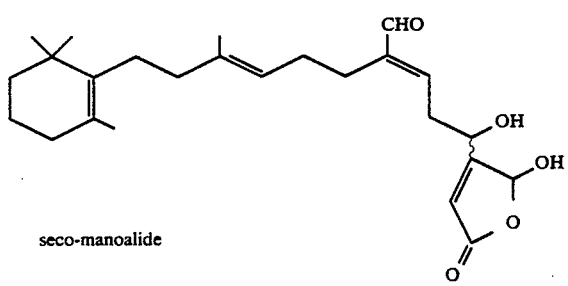

seco-manoalide

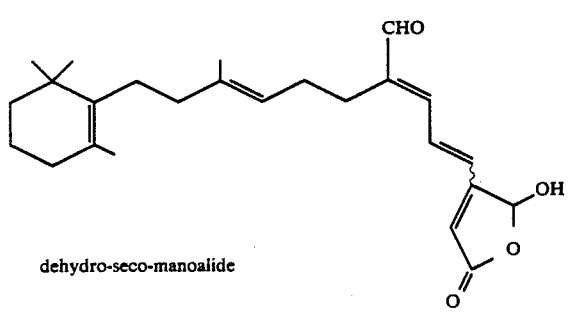

dehydro-seco-manoalide

THE INVENTION

The compounds of the present invention are represented by the following formula:

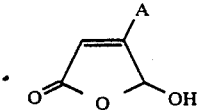

FORMULA I in which:
A is $CH_2-CO_2M$, $CH_2CH_2OCOR$, $(CH_2)_nCH=CHCOR$, $(CH_2)_qCOR$, $CH_2C(OH)R_3$, $CH_2CCH_2CO_2R$, $CH_2COCH=CHR$,
                            |           |
                            R           $R_3OCO$ $CH_2CH_2CHCO_2R_1$, $CH_2CH=CCO_2R_1$, $CHCO_2R_1$ $(CH_2)_mOX$,
         |                    |              |
         R                    R              R $(CH_2)_mCO_2R_1$, $CH_2C\equiv CCOR_2$, $CH_2CCH=CCO_2R_1$,
                                              |
                                              $CO_2R$ $CH_2CON-CH_2CH_2R_6$, $CH_2C=N-R_4$, or
        |                     |
        $R_1$                 $R_5$ $CH_2CH_2CHCH_2CO_2M$
         |
         $OCOR_3$ n is 1 or 2;
q is 1–4;
m is 8–12;
R is $C_7$–C alkyl, $C_7$–$C_{14}$ alkoxide, $NR_3(CH_2)_pZ$ or $C\equiv CM$;
p is 2–8;
Z is H, $N(R_3)_2$ or $CO_2H$;
$R_1$ is hydrogen or $C_1$–$C_4$ alkyl;
$R_2$ is $C_7$–C alkyl or phenyl;
M is $C_7$–$C_{14}$ alkyl; phenyl($C_1$–$C_4$ alkyl) optionally substituted on the phenyl ring by 1–3 halo substituents; pyridyl($C_1$–$C_4$ alkyl) or naphthyl($C_1$–$C_6$ alkyl);
$R_4$ is O($C_8$–$C_{14}$ alkyl) or NH($C_8$–$C_{14}$ alkyl); and $R_5$ is hydrogen or $R_4$ is OH and $R_5$ is o-hydroxyphenyl;
X is hydrogen or a group which will form an ester with the oxygen to which it is attached to increase water solubility, such as acetyl, $PO(OH)_2$, $CO(CH_2)_3N(R_3)_2$, or $CO(CH_2)_3N(R_3)_2 \cdot HCl$ or another pharmaceutically acceptable salt;
$R_3$ is $C_1$–$C_4$ alkyl; and $R_6$ is phenyl or $C_4$–$C_{12}$ alkyl.

The hydroxy group in the 5-position on the furanone ring may be acylated or alkylated by standard procedures, for example, by reacting the hydroxyfuranone with an acyl anhydride or halide or with an alkyl halide to give compounds also having anti-inflammatory activity as do the 5-hydroxyfuranones.

Particular compounds of this invention are represented by Formula I in which:
A is $CH_2CO_2M$, $CH_2CH_2OCOR$, $(CH_2)_nCH=CHCOR$ or $CHCO_2R_1$
|
R A preferred A group is $CH_2CH=CHCOR$.
Specific compounds of this invention are, for example:
4-(5-oxo-3-hexadecenyl)-5-hydroxy-2(5H)-furanone, 4-(3-dodecanoyloxypropyl)-5-hydroxy-2(5H)-furanone, 4-(2-carbomethoxytridecyl)-5-hydroxy-2(5H)-furanone and
4-(2-carbooctanoxyethyl)-5-hydroxy-2(5H)-furanone.

Certain of the compounds of this invention contain chiral centers and accordingly, may be prepared as enantiomeric or diasteriomeric mixtures or in optically pure form. Unless otherwise specified herein, such preparations are racemates at each chiral center. However, the scope of the invention is not to be considered as limited to these forms but also to encompass the individual optical isomers of the compounds.

Compounds of the invention are prepared from 5-trimethylsilyl(TMS)-3-furaldehyde by procedures which are graphically illustrated here and described in more detail in the examples.

oxygen and irradiating using an initiator such as Rose Bengal.

The 5-trimethylsilyl-3-furaldehyde starting material may be prepared by brominating 3-furaldehyde to give 5-bromo-3-furaldehyde which is converted to the dimethylacetal, then treated with t-butyl lithium and trimethylsilyl chloride. A preferred method for preparing 5-trimethylsilyl-3-furaldehyde is by reacting lithium morpholide and with 5-bromo-3-furaldehyde to protect the aldehyde group, then reacting with t-butyl lithium and trimethylsilyl chloride to give 5-trimethylsilyl-3-furaldehyde.

An improved method for preparing 5-trimethylsilyl-3-furaldehyde consists of reacting lithium morpholide with 3-furaldehyde, followed by secondary-butyl lithium, followed by trimethylsilyl chloride. The method is

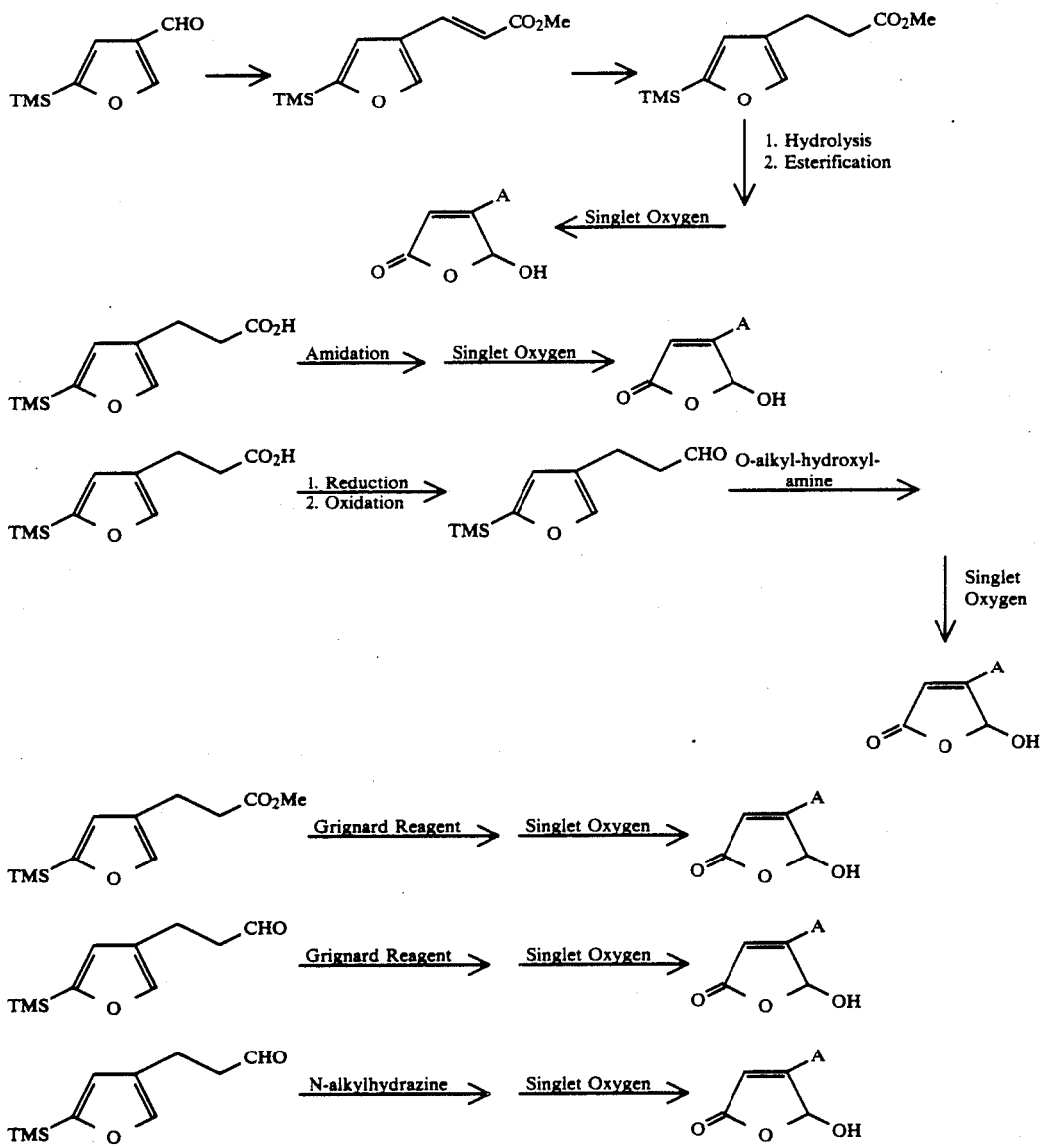

The aldehyde group of 5-trimethylsilyl-3-furaldehyde is converted to the desired CH$_2$—A group by procedures known to the art or described in the following examples to give 2-TMS-4-(CH$_2$—A)-furan intermediates. These intermediates are converted to the 5-hydroxy-4-(CH$_2$—A)-2-furanones by treating with also advantageous for the preparation of 5-triethylsilyl-3-furaldehyde using triethylsilyl chloride. 5-triethylsilyl-3-furaldehyde is useful as an intermediate in place of the trimethyl compound in methods described herein for preparing compounds of this invention.

The pharmaceutically acceptable, nontoxic, acid addition salts having the utility of the free bases of these compounds are formed with inorganic or organic acids, for example maleic, fumaric, benzoic, ascorbic, pamoic, succinic, methanesulfonic, acetic, propionic, tartaric, salicylic, citric, gluconic, aspartic, stearic, palmitic, glycolic, p-aminobenzoic, glutamic, benzenesulfonic, hydrochloric, hydrobromic, sulfuric, cyclohexylsulfamic, phosphoric and nitric acids. This is not intended to be an exhaustive list. Such salts can be prepared by methods well known in the art.

In addition, this invention relates to pharmaceutical compositions containing the compounds of Formula I as active ingredients and to methods of using the compounds and pharmaceutical compositions of this invention to produce anti-inflammatory, immunosuppressant and anti-proliferative activity. These compounds are useful in treating inflammation, in suppressing unwanted immune responses and in retarding proliferation of cells. Uses include treatment of rheumatoid arthritis, osteoarthritis, rheumatic carditis and autoimmune diseases such as allergic diseases, bronchial asthma and myasthenia gravis and ocular and dermal inflammatory diseases. The compounds are useful in treating psoriasis, acne, atopic diseases and allergic conjunctivitis. They are also useful as adjuvant therapy associated with organ and tissue transplants.

The activity of the compounds of this invention is demonstrated by inhibition of the enzyme phospholipase $A_2$ in vitro and by reduction of inflammation in the mouse ear anti-inflammatory assay in vivo.

The compound also inhibit phosphoinositide-specific phospholipase C. This activity has been reported for manoalide and may indicate anti-inflammatory utility. Bennett et al, *Molecular Pharmacology* 32:587–593 (1987).

The compounds also inhibit ornithine decarboxylase, a rate limiting enzyme in cellular growth, which indicates use in treating psoriasis and neoplasis.

The compounds also modify calcium homeostasis. This activity is shown by effect on intracellular calcium levels in experiments using gastric glands, spleen cells, epithelial cells, $GH_3$ cells. etc. Calcium is inhibited from entering through the plasma membrane calcium channels and calcium release from intercellular stores is also blocked. Modification of calcium homeostasis is expected to have application in diseases of the nervous system involving modification of membrane lipids or transmitter release (Parkinson's, Alzheimer's), diseases of the cardiovascular system involving application of cardiac or vascular smooth muscle contractility and platelet aggregation (hypertension, cardiac infarction and atherosclerosis), diseases of the gastrointestinal tract such as ulcer disease, diarrhea, motility due to secretion of acid or chloride ion, diseases of the kidney involving renal handling of fluid and electrolytes (metabolic acidosis, alkalosis), and diseases of abnormal growth (neoplasia, psoriasis).

The compounds of this invention have activity which is similar to that of manoalide, that is the compounds appear to be devoid of the endocrine properties of the glucocorticoids while having anti-inflammatory and immunosuppresive properties.

In the methods of this invention, the compounds of the invention are administered to mammals, including humans, in an effective amount of about 0.05 to 100 mg per day per kilogram of body weight. The amount of the compound depends upon the disease or condition being treated, the severity thereof, the route of administration and the nature of the host. The compounds may be administered topically, orally, parenterally or by other standard routes of administration.

Pharmaceutical compositions of this invention comprise compounds of Formula I and pharmaceutical carriers suitable for the route of administration. Standard methods for formulating pharmaceutical composition of this type may be found in *Remington's Pharmaceutical Sciences*, Mack Publishing Company, Easton, PA.

For topical administration, the pharmaceutical composition may be in the form of a salve, cream, ointment, spray, powder or the like. Standard pharmaceutical carriers for such compositions may be used. Preferably, compositions for topical administration will contain 0.05–5% of the active ingredient.

A typical cream formulation may contain the following:

| Ingredient | Parts by Weight |
| --- | --- |
| Water/glycol mixture (15% or more glycol) | 50–99 |
| Fatty alcohol | 1–20 |
| Non-ionic surfactant | 0–10 |
| Mineral oil | 0–10 |
| Typical pharmaceutical adjuvants | 0–5 |
| Active ingredient | 0.05–5 |

A typical ointment formulation may contain the following:

| Ingredients | Parts by Weight |
| --- | --- |
| White petrolatum | 40-94 |
| Mineral oil | 5-20 |
| Glycol solvent | 1-15 |
| Surfactant | 0-10 |
| Stabilizer | 0-10 |
| Active ingredient | 0.05-5 |

For oral administration, suitable pharmaceutical carriers include mannitol, lactose, starch, magnesium stearate, talcum, glucose and magnesium carbonate. Oral compositions may be in the form of tablets, capsules, powders, solutions, suspensions, sustained release formulations, and the like.

A typical tablet or capsule may contain the following:

| Ingredients | Percent w/w |
| --- | --- |
| Lactose, spray-dried | 40–99 |
| Magnesium stearate | 1–2 |
| Cornstarch | 10–20 |
| Active ingredient | 0.001–20 |

Parenteral compositions are prepared in conventional suspension or solution forms, as emulsions or as solid forms for reconstruction. Suitable carriers are water, saline, dextrose, Hank's solution, Ringer's solution, glycerol, and the like. Parenteral administration is usually by injection which may be subcutaneous, intramuscular or intravenous.

The compounds of this invention may be combined with other known anti-inflammatory/immunosuppressive agents such as steroids or non-steroidal anti-inflammatory agents (NSAID) in the pharmaceutical compositions and methods described herein.

The following examples are intended to illustrate the invention but are not limiting. All temperatures are in degrees Centigrade. NMR data are recorded in delta ppm.

Preparation of Intermediate
5-Trimethylsilyl-3-furaldehyde n-Butyl lithium (a 1.6M solution in hexane; 31.0 ml, 49.7 mmol) was added dropwise to a solution of morpholine (4.33 ml, 49.7 mmol; freshly distilled from barium oxide) in tetrahydrofuran at −78° under argon. After 15 minutes, a solution of 5-bromo-3-furaldehyde (7.5 g, 49.7 mmol) in tetrahydrofuran was added dropwise. Stirring was continued for 30 min. and n-butyl lithium (a 1.6M solution in hexane; 46.6 ml, 74.5 mmol) was added dropwise. After 1 hour at −78°, chlorotrimethylsilane (18.9 ml, 149 mmol) was added and stirring continued while the cooling bath attained room temperature. The reaction mixture was quenched with 10% hydrochloric acid and the phases were separated. The aqueous phase was stirred, in the presence of ethyl ether (30 ml), with 10% hydrochloric acid at 0° C. for ½ hour. The organic phases were combined, washed (brin), dried (magnesium sulfate) and evaporated down. The residue was distilled under vacuum to give the title aldehyde as a colorless oil b.p. 48°–50°/0.25 torr.

$^1$H NMR (CDCl$_3$): 0.29(s,9H), 6.98(s,1H), 8.25 (s,1H) and 9.95 (s,1H)

$^{13}$CNMR (CDCl$_3$): −2.0, 116.2, 128.9, 155.3, 164.1 and 184.5.

MS m/e: Exact mass calculated for C$_8$H$_{12}$O$_2$Si: 168.0607, found 168.0588.

Alternative Preparation of Intermediate
5-trimethylsilyl-3-furaldehyde n-Butyl lithium (a 2.5 m solution in hexane; 28.8 ml, 72 mmol) was added to a solution of morpholine (6.28 ml, 72 mmol) in tetrahydrofuran (700 ml) at −78° under argon. After 20 minutes, 3-furaldehyde (7.0 g, 72 mmol) was added. After another 20 minutes, sec-butyl lithium (a 1.3 m solution in cyclohexane; 55.4 ml, 72 mmol) was added dropwise and stirring continued at −78° for 7 hours before trimethylsilyl chloride (27 ml, 216 mmol) was added. Stirring was continued overnight (14 hours) while the cooling bath was allowed to attain room temperature. The solution was poured into ice cold 10% (v/v) hydrochloric acid (200 ml) and after stirring at 0° for 10 minutes, the layers were separated. The aqueous phase was extracted with diethyl ether. All the organic phases were combined, dried (magnesium sulfate) and evaporated down to give a light brown oil, which was purified by flash chromatography on silica using 2% ethyl ether/hexane. Fractions with R$_f$ of about 0.30 (silica, 10% ethyl ether/hexane) on evaporation gave the title aldehyde as a light yellow oil, b.p. 48°–50°/0.25 torr.

$^1$H NMR(CDCl$_3$): 0.29 (s,9H), 6.98 (s,1H), 8.25 (s,1H) and 9.95 (s,1H).

$^{13}$C NMR (CDCl$_3$): −2.0, 116.2, 128.9, 155.3, 164.1 and 184.5.

EXAMPLE 1

Octyl 3-(5-trimethylsilyl-3-furyl)propen-2-oate

Lithium diisopropylamide (a 1.5M solution in cyclohexane; 1.34 ml, 2.0 mmol) was added dropwise to a solution of octyl acetate (322.2 mg, 193 mmol) in tetrahydrofuran (7 ml) at −78° under argon. After 20 minutes, a solution of 5-trimethylsilyl-3-furaldehyde (324 mg, 1.93 mmol) in tetrahydrofuran (1 ml) was added. Stirring was continued at −78° for 1 hour and trifluoromethanesulfonic anhydride (0.65 ml, 3.86 mmol) was added. After 1 hour, 1,8-diazobicyclo[5.4.0]undec-7-ene (0.58 ml, 3.86 mmol) was added and stirring was continued overnight while the cooling bath attained room temperature. The mixture was diluted with ether (30 ml) and acidified with diluted HCl. Extraction (ethyl ether), washing of the extracts (brine), drying (magnesium sulphate) and evaporation afforded an oil, which was subjected to flash chromatography (silica). Elution with 10% ethyl ether/hexane gave octyl 3-(5-trimethylsilyl-3-furyl) propen-2-oate as a light yellow oil.

$^1$H NMR (CDCl$_3$): 0.29 (s, 9H), 0.91 (t, 3H, J=6.9 Hz), 1.30 (brs, 10H), 1.70 (m, 2H), 4.18 (t, 2H, J=6.8 Hz), 6.17 (d, 1H, J=15.0 Hz), 6.80 (s, 1H), 7.60 (d, 1H, J=15.6 Hz), and 7.84 (s, 1H).

MS m/e (% abundance): 323 (M$^+$+1, 20), 322 (M$^+$, 47), 307 (15), 210 (36), 195 (61), 166 (70) and 73 (100).

Octyl 3-(5-trimethylsilyl-3-furyl)propionate

A solution of octyl 3-(5-trimethylsilyl-3-furyl)propen-2-oate (175 mg, 0.5 mmol) in ether (10 ml) was hydrogenated over platinum (IV) oxide (ca. 10 mg) at room temperature for 1½ hours. The mixture was filtered through celite and the filtrate on evaporation gave an oil, which was flash chromatographed on silica using 5% ethyl ether/petroleum ether. Fraction with R$_f$ of about 0.39 on evaporation afforded the title ester as a pale yellow oil.

$^1$H NMR (CDCl$_3$): 0.25 (s, 9H), 0.90 (t, 3H, J=6.9 Hz), 1.29 (brs, 10H), 1.60 (br, 2H), 2.57 (t, 2H, J=7.2 Hz), 2.77 (t, 2H, J=6.9 Hz), 4.08 (t, 2H, J=6.7 Hz), 6.51 (s, 1H) and 7.44 (s, 1H).

MS m/e (% abundance): 324 (M$^+$, 32), 309 (10), 212 (19), 197 (19), 167 (34), 155 (48) and 73 (100).

4-(2-Carbooctanoxyethyl)-5-hydroxy-2(5H)-furanone

A mixture of octyl 3-(5-trimethylsilyl-3-furyl)-propionate (117.1 mg, 0.36 mmol) and Rose Bengal (3 mg) in tetrahydrofuran (8 ml) was exposed to singlet oxygen for 2 hours at −78°. The residue, after solvent removal, was flash chromatographed on silica using 60% ethyl ether/petroleum ether. Fractions with R$_f$ of about 0.13 on evaporation afforded the 4-(3-carbooctanoxy)ethyl-5-hydroxy-2(5H)-furanone as a pale yellow oil.

$^1$H NMR (CDCl$_3$): 0.91 (t, 3H, J=7.2 Hz), 1.30 (brm, 12H), 1.65 (t, 2H, J=7.0 Hz), 2.73 (p and t, 4H), 4.12 (t, 2H, J=5.6 Hz), 5.89 (d, 1H, J=0.9 Hz) and 7.29 (d, 1H, J=1.2 Hz). $^{13}$C NMR (CDCl$_3$): 14.1, 22.5, 22.6, 25.8, 28.5, 29.1, 31.6, 31.8, 65.6, 99.2, 118.2, 167.6, 170.8 and 172.6.

MS m/e: exact mass calculated for C$_{15}$H$_{25}$O$_5$ (M+H)$^+$ 285.1702, found 285.1700.

EXAMPLE 2

Methyl 3-(5-trimethylsilyl-3-furyl)propen-2-oate

A mixture of methyl(triphenylphosphoranylidene) acetate (994 mg, 2.97 mmol) and 5-trimethylsilyl-3 -furaldehyde (384 mg, 2.29 mmol) in tetrahydrofuran (10 ml) was stirred at room temperature for 48 hours. The reaction mixture was evaporated with a minimum amount of silica and the residue was flash chromatographed on silica using 5% ethyl ether/petroleum ether. Fraction with R$_f$ of about 0.16 on evaporation afforded the title ester as a pale yellow oil.

¹H NMR (CDCl₃): 0.39 (s, 9H), 3.79 (s, 3H), 6.15 (d, 1H, J=15.9 Hz), 6.79 (s, 1H), 7.60 (d, 1H, J=15.9 Hz) and 7.83 (s, 1H).

¹³C NMR (CDCl₃): −2.0, 51.3, 116.7, 122.5, 134.9, 148.6, 162.8 and 167.4.

MS m/e: Exact mass calculated for C₁₁H₁₆O₃Si (M+):224.0868, found 224.0875.

Methyl 3-(5-trimethylsilyl-3-furyl)propionate

A solution of methyl3-(5-trimethylsilyl-3-furyl)propen-2-oate (107.7 mg, 0.48 mmol) in ethyl ether (5 ml) was hydrogenated over platinum (IV) oxide (ca. 10 mg) at room temperature for 14 hours. The mixture was filtered through celite and the filtrate on evaporation gave the desired ester, which was used directly in the next step.

¹H NMR (CDCl₃): 0.24 (s, 9H), 2.57 (t, 2H, J=6.7 Hz), 2.76 (t, 2H, J=6.7 Hz), 3.69 (s, 3H), 6.49 (s, 1H) and 7.43 (s, 1H).

¹³C NMR (CDCl₃): −1.8, 20.0, 34.6, 51.4, 120.7, 123.3, 143.1, 160.6 and 173.2.

MS m/e: Exact mass calculated for C₁₁H₁₈O₃Si (M+): 226.1025, found 226.1034.

3-(5-Trimethylsilyl-3-furyl)propan-1-ol

A solution of methyl 3-(5-trimethylsilyl-3-furyl)propionate (from above) in tetrahydrofuran (3 ml) was added dropwise to a suspension of lithium aluminum hydride (27 mg) in tetrahydrofuran (4 ml) at room temperature. After 3 hours, the mixture was quenched with ethyl acetate and extracted with ether. Evaporation of the dried (magnesium sulphate) extracts gave the title alcohol, which was used in the next step without purification.

¹H NMR (CDCl₃): 0.25 (s, 9H), 1.65 (br, 1H), 1.84 (p, 2H, J=7.3 Hz), 2.52 (t, 2H, J=7.8 Hz), 3.69 (t, 2H, J=6.3 Hz), 6.51 (s, 1H) and 7.42 (s, 1H).

MS m/e (% abundance): 198 (M+, 11), 154 (70), 139 (26), 101 (26), 73 (79).

3-(5-Trimethylsilyl-3-furyl)propyl dodecanoate

Pyridine (0.06 ml, 0.72 mmol) was added to a mixture of 3-(5-trimethylsilyl-3- furyl)propan-1-ol (from above) and lauroyl chloride (0.17 ml. 0.72 mmol) in tetrahydrofuran (4 ml) at room temperature. After 14 hours, the mixture was diluted with ether (10 ml) and washed successively with water, copper (II) sulphate and brine. Evaporation of the dried (magnesium sulphate) organic layers gave an oil, which was purified by preparative TLC (20×20 cm, 500μ silica plate; developed with 10% ethyl ether/petroleum ether). The title ester was obtained as a colorless oil.

¹H NMR (CDCl₃): 0.28 (s, 9H), 0.92 (t, 3H, J=7.3 Hz), 1.29 (brs, 18H), 1.65 (m, 2H), 1.92 (p, 2H, J=7.4 Hz), 2.33 (m, 2H), 2.53 (t, 2H, J=7.9 Hz), 4.13 (m, 2H), 6.53 (s, 1H) and 7.45 (s, 1H).

MS m/e (% abundance): 381 (M++1, 13), 365 (4), 183 (29), 180 (100), 154 (33), 101 (52) and 73 (64).

4-(3-Dodecanoyloxypropyl)-5-hydroxy-2(5H)-furanone

A mixture of 3-(5-trimethylsilyl-3-furyl)propyl dodecanoate (105 mg, 0.27 mmol) and Rose Bengal (5 mg) in tetrahydrofuran (6 ml) was exposed to singlet oxygen for 2.5 hours at −78°. The residue, after solvent removal, was purified by preparative thin layer chromatography (TLC) (20×20 cm, 500μ silica plate; developed with 60% ethyl ether/petroleum ether). The title ester was obtained as an off-white solid.

¹H NMR (CDCl₃): 0.89 (t, 3H, J=6.9 Hz), 1.27 (brs, 18H), 1.60 (m, 2H), 1.99 (p, 2H, J=7.4 Hz), 2.32 (t, 2H, J=7.7 Hz), 2.52 (brt, 2H), 4.17 (t, 2H, J=6.3 Hz), 5.91 (s, 1H), and 6.03 (s, 1H).

¹³C NMR (CDCl₃): 14.1, 22.7, 24.3, 24.9, 25.8, 29.1, 29.3, 29.5, 29.6, 31.9, 34.3, 63.1, 99.2, 117.8, 168.6, 171.3 and 174.3.

MS m/e: Exact mass calculated for C₁₉H₃₆NO₅ (M+NH₄)+: 358.2593, found 358.2583.

EXAMPLE 3

3-(2-Trimethysilyl-4-furyl)propan-1-al

To a stirring mixture of pyridinium chlorochromate (3.89 g, 18.03 mmol) suspended in methylene chloride (100 ml) at 0° was added 3-(2-trimethylsilyl-4-furyl)propan-1-ol (1.19 g. 6.01 mmol), prepared as in Example 2, in dry methylene chloride (15 ml). This mixture was allowed to warm to room temperature, stirred for 90 minutes, filtered and concentrated to give the desired aldehyde.

IR (CHCl₃): 3020, 1720, 1220 cm⁻¹.

¹H NMR (CDCl₃): 9.82 (s, 1H); 7.42 (s, 1H); 6.48 (s, 1H), 2.65 to 2.85 (m, 4H); 0.24 (s, 9H).

¹³C NMR (CDCl₃): 201.8, 161.1, 143.2, 123.2, 120.7, 44.1, 17.3, −1.7.

MS m/e: calculated for C₁₀H₁₆O₂Si(M+): 196.0919, found 196.0943.

Dimethyl-2-oxotridecylphosphonate

To a stirred solution of methyl laurate (1.5 g, 7.0 mmol) in tetrahydrofuran (120 ml) at −78° was added the lithium salt of dimethylmethylphosphonate (0.901 g, 7.26 mmol; generated with n-butyl lithium (5.29 ml of a 1.39M solution in hexane). The stirring mixture was warmed to room temperature over four hours and partitioned between ethyl ether and 5% aqueous ammonium chloride solution. The organic portion was washed with 5% sodium bicarbonate, water, saturated sodium chloride solution, dried over magnesium sulfate, filtered and concentrated to give a colorless oil. Purification by flash chromatography (silica, 80% to 90% ethyl acetate/hexane) gave the desired phosphonate ester.

IR (CHCl₃): 2920, 2850, 1710, 1250 cm⁻¹.

¹H NMR (CDCl₃): 3.81 (s, 3H); 3.77 (s, 3H); 3.09 (d, J=22.7 Hz, 2H); 2.61 (t, J=7.3 Hz, 2H); 1.51 to 1.62 (m, 2H); 1.20–1.35 (m, 16H); 0.88 (t, J=6.7 Hz, 3H).

¹³C NMR (CDCl₃): 201.9, 52.9, 52.8, 44.1, 42.0, 40.2, 31.8, 29.5, 29.2, 28.9, 28.8, 23.3, 22.5, 14.0.

MS m/e: Calculated for C₁₅H₃₁O₄P(M+): 306.1960, found 306.1963.

4-(5-Oxo-3-hexadecenyl)-2-trimethylsilylfuran

To sodium hydride (0.016 g, 0.677 mmol) under argon was added dimethyl-2-oxotridecylphosphonate (0.207 g, 0.677 mmol) in tetrahydrofuran (5 ml). The mixture was stirred for 20 minutes at room temperature, followed by the addition of 3-(2-trimethylsilyl-4-furyl)-propan-1-al (0.111 g, 0.564 mmol) in tetrahydrofuran (5 ml). After stirring for five hours the reaction was quenched with 10% aqueous hydrochloric acid and extracted with ethyl ether. The organic portion was washed with 5% sodium bicarbonate, water, saturated sodium chloride solution, dried over magnesium sulfate, filtered and concentrated to give an oil. Purification by flash chromatography (silica, 3% to 5% ethyl acetate/hexane) gave the desired enone.

IR (CHCl₃): 2940, 1660, 1250 cm⁻¹.

¹H NMR (CDCl₃): 7.41 (s, 1H); 6.77 to 6.90 (m, 1H); 6.49 (s, 1H); 6.13 (d, J=16.0 Hz, 1H); 2.42 to 2.65 (m, 6H); 1.59 (t, J=7.1 Hz, 2H), 1.21 to 1.35 (m, 16H); 0.89 (t, J=6.7 Hz, 2H); 0.25 (s, 9H).

¹³C NMR (CDCl₃): 200.9, 160.8, 145.9, 143.1, 130.6, 123.6, 120.7, 40.2, 32.8, 31.9, 29.6, 29.4, 29.3, 24.3, 23.3, 22.6, 14.0, −1.7.

MS m/e: Calculated for C₂₃H₄₀O₂Si(M+): 376.2797, found 376.2808.

4-(5-Oxo-3-hexadecenyl)-5-hydroxy-2(5H)-furanone

A stirred solution of 4-(5-oxo-3-hexadecenyl)-2-trimethylsilylfuran (47 mg, 0.125 mmol) and Rose Bengal in acetone (2 ml) was flushed with oxygen and cooled to −78°. The solution was subsequently irradiated with a 150 watt flood lamp while under constant, positive pressure of oxygen until starting material was no longer visible by TLC. The solution was warmed to room temperature, concentrated and passed through silica (40% ethyl acetate/hexane) to give a pale red solid. This material was further purified by recrystallization (hexane/ethyl ether) to give the desired hydroxybutenolide.

IR (CHCl₃): 3340 (broad), 2920, 1750, 1630 cm⁻¹.

¹H NMR (CDCl₃): 6.83 (dt, J=16 Hz, J=5.8 Hz, 1H); 6.19 (d, J=16 Hz, 1H), 6.13 (broad s, 1H); 6.06 (s, 1H); 5.87 (s, 1H), 2.45 to 2.75 (m, 6H), 1.59 (t, J=7.0 Hz, 2H), 1.15 to 1.40 (m, 16H), 0.88 (t, J=6.7 Hz, 3H).

¹³C NMR (CDCl₃): 201.5, 171.5, 168.2, 144.4, 131.0, 117.9, 99.2, 40.5, 31.8, multiple peaks from 29.0 to 29.5, 25.9, 24.1, 22.6. 14.0.

MS m/e: calculated for C₂₀H₃₆O₄N(M+NH₄)+: 354.2644, found 354.2658.

EXAMPLE 4

4-(5-Oxohexadecyl)-2-trimethylsilylfuran

To 4-(5-oxo-3-hexadecenyl)-2-trimethylsilylfuran (98 mg, 0.261 mmol), prepared as in Example 3, in ethyl acetate (2 ml) was added platinum oxide (10 mg, 0.044 mmol). This mixture was subjected to one atmosphere of hydrogen at room temperature with stirring for 2½ hours. The reaction mixture was filtered and concentrated to give a yellow oil. Purification by flash chromatography (silica, 3% ethyl ether/hexane) gave the desired ketone.

IR (CHCl₃): 2920, 1700 cm⁻¹.

¹H NMR (CDCl₃): 7.39 (s, 1H); 6.48 (s, 1H); 2.27 to 2.50 (m, 6H); 1.50 to 1.70 (m, 6H); 1.10 to 1.40 (m, 16H); 0.88 (t, J=6.6 Hz, 3H); 0.24 (s, 9H).

¹³C NMR (CDCl₃): 211.3, 160.4, 142.9, 124.7, 121.0, 42.8, 42.7, 31.9, 29.7, 29.6, 29.4, 29.2, 24.2, 23.8, 23.5, 22.7, 14.1, −1.7.

MS m/e: calculated for C₂₃H₄₂O₂Si(M+): 378.2954, found 378.2968.

4-(5-Oxohexadecyl)-5-hydroxy-2(5H)-furanone

A stirred solution of 4-(5-oxohexadecyl)-2-trimethylsilylfuran (71 mg, 0.187 mmol) and Rose Bengal in acetone (20 ml) was flushed with oxygen and cooled to −78°. The solution was subsequently irradiated with a 150 watt flood lamp while under constant positive pressure of oxygen until no starting material remained. The solution was warmed to room temperature, concentrated and filtered through silica to give a pale red solid. Purification by flash chromatography (silica, 40% ethyl acetate/hexane) gave the desired hydroxybutenolide.

IR (CHCl₃): 3360 (broad), 2920, 1740, 1705 cm⁻¹.

¹H NMR (CDCl₃): 6.04 (d, J=5.5 Hz, 1H); 5.80 to 5.90 (m, 2H); 2.32 to 2.57 (m, 6H); 1.50 to 1.73 (m, 6H), 1.20 to 1.40 (m, 16H); 0.88 (t, J=6.7 Hz, 3H).

¹³C NMR (CDCl₃): 212.1, 171.9, 169.7, 117.4, 99.3, 43.0, 42.0, 31.9, 29.6, 29.4, 29.3, 29.2.

MS m/e: Calculated for C₂₀H₃₄O₄ (M+): 338.2457, found 338.2449.

EXAMPLE 5

Triethyl 1-decylphosphonoacetate

To a suspension of sodium hydride (0.321 g, 13.38 mmol) in tetrahydrofuran (30 ml) at room temperature was added triethylphosphonoacetate (2.0 g, 8.92 mmol). After stirring for 15 minutes to this mixture was added 1-bromodecane (2.17 g, 9.81 mmol) and sodium iodide (0.30 g, 2.00 mmol). After refluxing for 18 hours the reaction was quenched with 10% aqueous hydrochloric acid and extracted into ethyl ether. The organic portion was washed with 5% sodium bicarbonate, water, saturated sodium chloride solution, dried over magnesium sulfate, filtered and concentrated to give a yellow oil. Purification by flash chromatography (silica, 30% to 50% ethyl acetate/hexane) gave the desired phosphonate ester.

IR (CHCl₃): 3010, 2920, 1720, 1230 cm⁻¹.

¹H NMR (CDCl₃): 4.08 to 4.26 (m, 6H), 2.86 to 2.92 (ddd, J=10.9 Hz, 22.5 Hz, 3.8 Hz, 1H); 1.75 to 1.90 (m, 1H); 1.90 to 2.05 (m, 1H); 1.20 to 1.40 (m, 25H); 0.88 (t, J=6.6 Hz, 3H).

¹³C NMR (CDCl₃): 168.6, 62.1, 62.0, 61.9, 60.6, 46.2, 44.4, 31.4 multiple peaks from 26.4 to 29.0, 22.1, 15.9, 15.8, 13.6, 13.5.

MS m/e: Calculated for C₁₈H₃₈O₅P (MH)+: 365.2457, found 365.2465.

(E)-Ethyl 2-decyl-5-(2-trimethylsilyl-4-furyl)penten-2-oate and (Z)-Ethyl 2-decyl-5-(2-trimethylsilyl-4-furyl)penten-2-oate To sodium hydride (0.111 g, 2.78 mmol) under argon was added triethyl 1-decylphosphonoacetate (0.813 g, 2.32 mmol) in tetrahydrofuran (10 ml). The mixture was stirred for 10 minutes at room temperature, followed by the addition of 3-(2-trimethylsilyl-4-furyl)propan-1-al (0.455 g, 2.32 mmol). After 10 minutes the reaction was quenched with 10% aqueous hydrochloric acid and extracted with ethyl ether. The organic portion was washed with 5% sodium bicarbonate, water, saturated sodium chloride solution, dried over magnesium sulfate, filtered and concentrated to give a yellow oil. Purification by preparative TLC (silica, 3% ethyl acetate/hexane) afforded the desired E and Z isomers.

(Z)-Ethyl 2-decyl-5-(2-trimethylsilyl-4-furyl)penten-2-oate

IR (CHCl₃): 2930, 2860, 1695, 1250 cm⁻¹.

¹H NMR (CDCl₃): 7.24 (s, 1H); 6.75 (t, J=7.3 Hz, 1H); 6.50 (s, 1H); 4.19 (q, J=7.1 Hz, 2H); 2.50 to 2.62 (m, 2H); 2.38 to 2.48 (m, 2H); 2.27 (t, J=7.3, 2H); 1.20 to 1.50 (m, 19H); 0.88 (t, J=6.7 Hz, 3H); 0.25 (s, 9H).

¹³C NMR (CDCl₃): 168.1, 160.7, 143.1, 141.1, 133.3, 124.1, 60.4. 31.9, multiple peaks from 29.6 to 29.2, 26.8, 24.0, 22.7, 18.0, 14.3, 14.1, −1.7.

MS m/e: Calculated for C₂₄H₄₂O₃Si(M+): 406.2903, found 406.2892.

(E)-Ethyl 2-decyl-5-(2-trimethylsilyl-4-furyl)penten-2-oate

IR (CHCl$_3$): 2920, 2850, 1695, 1245 cm$^{-1}$.

$^1$H NMR (CDCl$_3$): 7.41 (s, 1H); 6.50 (s, 1H); 5.85 (t, J=7.1 Hz, 1H); 4.18 (q, J=7.1 Hz, 2H); 2.61 to 2.73 (m, 2H); 2.49 to 2.60 (m, 2H); 2.23 (t, J=7.3 Hz, 2H); 1.15 to 1.50 (m, 19H); 0.89 (t, J=5.8 Hz, 3H); 0.26 (s, 9H).

$^{13}$C NMR (CDCl$_3$): 168.2, 160.3, 143.1, 140.0, 133.0, 124.3, 121.1, 60.0, 34.5, 31.9, multiple peaks from 28.7 to 29.9, 24.5, 22.7, 14.3, 14.1, −1.6.

MS m/e: calculated for C$_{24}$H$_{42}$O$_3$Si(M+): 406.2903, found 406.2898.

4-(4-Carboethoxytetradecyl)-2-trimethylsilylfuran

To a stirred solution of (Z)-ethyl 2-decyl-5-(2-trimethylsilyl-4-furyl)penten-2-oate (99 mg, 0.244 mmol) in ethyl acetate (5 ml) was added platinum oxide (28 mg, 0.122 mmol). This mixture was subjected to one atmosphere of hydrogen for 18 hours, then filtered and concentrated to give an oil. Purification by flash chromatography (silica, 0% to 3% ethyl ether/hexane) gave the desired ester.

IR (CHCl$_3$): 2920, 2850, 1700 cm$^{-1}$.

$^1$H NMR (CDCl$_3$): 7.39 (s, 1H); 6.47 (s, 1H); 4.14 (q, J=7.0 Hz, 2H); 2.27 to 2.44 (m, 3H); 1.37 to 1.70 (m, 6H); 1.15 to 1.36 (m, 19H); 0.88 (t, J=6.5 Hz, 3H); 0.24 (s, 9H).

$^{13}$C NMR (CDCl$_3$): 176.4, 160.4, 143.0, 124.7, 121.0, 60.0, 45.6, 32.5, 32.3, 32.1, 31.9, 29.8, 29.6, 29.5, 29.3, 27.9, 27.4, 24.5, 22.7. 14.3, 14.1, −1.6.

MS m/e: Calculated for C$_{24}$H$_{44}$O$_3$Si(M+): 408.3060, found 408.3065.

4-(4-Carboethoxytetradecyl)-5-hydroxy-2(5H)-furanone

A stirred solution of 4-(4-carboethoxytetradecyl)-2-trimethylsilylfuran (50 mg, 0.123 mmol) and Rose Bengal in acetone (25 ml) was flushed with oxygen and cooled to −78°. The solution was subsequently irradiated with a 150 watt-flood lamp while under constant, positive pressure of oxygen until no starting material was visible by TLC. The solution was warmed to room temperature and concentrated to give a red oil. Purification by preparative TLC (silica, 30% ethyl acetate/hexane) gave the desired hydroxybutenolide.

IR (CHCl$_3$): 3340 (broad), 2920, 2825, 1720 cm$^{-1}$.

$^1$H NMR (mixture of diastereomers), (CDCl$_3$): 6.01 (s, 1H); 5.84 (s, 1H); 5.29 (broad s, 1H); 4.15 (q, J=7.1 Hz, 2H); 2.25 to 2.51 (m, 3H); 1.15 to 1.75 (m, 25H); 0.88 (t, J=6.7 Hz, 3H).

$^{13}$C NMR (mixture of diastereomers), (CDCl$_3$): 176.6, 171.6, 169.3, 117.6, 99.1, 60.5, 45.5, 32.6, 31.9, 31.7, multiple peaks between 29.3 and 29.6, multiple peaks between 27.3 and 27.6, 24.5, 22.7, 14.3, 14.1.

MS m/e: Calculated for C$_{21}$H$_{36}$O$_5$(M+): 368.2563, found 368.2558.

EXAMPLE 6

(E)-1-(2-Trimethylsilyl-4-furyl)-2-carbomethoxy-tridec-1-ene

Potassium bis(trimethylsilyl)amide (a 0.5M solution in toluene; 14.5 ml, 7.24 mmol) was added to a solution of dodecyltriphenylphosphonium bromide (1.82 g, 3.56 mmol) in tetrahydrofuran (10 ml) at −78° under argon. After one hour, methyl chloroformate (0.28 ml, 3.56 mmol) was added, followed by 5-trimethylsilyl-3-furaldehyde (300 mg, 1.78 mmol) after one hour. Stirring was continued overnight while the cooling bath attained room temperature. The mixture was quenched with methanol/water (30 ml, 1:1). Extraction (ethyl ether/hexane, 1:1) and evaporation of the dried (magnesium sulfate) extracts gave an oil, which was flash chromatographed on silica using 20% ethyl ether/hexane. The title ester was obtained as a pale yellow oil.

$^1$H NMR (CDCl$_3$): 7.8 (s, 1H), 7.5 (s, 1H), 6.75 (s, 1H), 3.77 (s, 3H), 3.65 (s. 1H), 2.5 (t, 2H, J=7.5 Hz), 2.3 (q, 2H. J=7.5), 1.3 (m, 18H), 0.87 (t, 3H, 7.5 Hz).

$^{13}$C NMR (CDCl$_3$): −1.8, 14.1, 22.6, 28.1, 28.6, 29.1, 29.2. 29.3, 29.4, 29.6, 29.8, 31.8, 51.8, 120.1, 121.6, 129.0, 131.0, 148.2, 162.1 and 168.9

MS m/e (% abundance): 379 (M+, 100), 363 (27), 347 (19), 323 (54), 275 (18), 229 (50), 183 (23), 105 (36) and 73 (17).

4-(2-carbomethoxytridecyl)-2-trimethylsilylfuran

A solution of (E)-1-(2-trimethylsilyl-4-furyl)-2-carbomethoxytridec-1-ene (133 mg, 0.35 mmole) in ethyl acetate (20 ml) was hydrogenated over 5% rhodium on alumina (ca 10 mg) at room temperature for 3 days. The mixture was filtered through celite and the filtrate on evaporation gave an oil which was purified by preparative TLC (20×20 cm, 1000μ silica plate; developed with 10% ethyl ether/hexane). The title ester was obtained as a colorless oil.

$^1$H NMR (CDCl$_3$): 7.4 (s, 1H), 6.43 (s, 1H), 3.62 (s, 3H), 2.75 (dd, 1H, J=7.5 Hz, J=15 Hz), 2.55 (m, 2H), 1.5 (m, 2H), 1.2 (m, 18H), 0.85 (t, 3H, J=7.5 Hz), 0.25 (s, 9H).

$^{13}$C NMR (CDCl$_3$): 71.1, 167.4, 158.6, 143.8, 125.4, 120.4, 99.2, 52.6, 31.8, 29.8, 29.6, 29.5, 29.3, 29.0, 28.7, 22.6, 14.1.

4-(2-Carbomethoxytridecyl)-5-hydroxy-2(5H)-furanone

A mixture of 4-(2-carbomethoxytridecyl)-2-trimethylsilylfuran (72 mg, 0.19 mmole) and Rose Bengal (5 mg) in acetone (10 ml) was exposed to singlet oxygen at −78° for four hours. The residue, after solvent removal, was purified by preparative TLC (20×20 cm, 1000μ silica plate; developed with 50% ethyl ether/hexane). The title furanone was obtained as a white solid.

$^1$H NMR (CDCl$_3$): 6.08 (s, 1H), 5.9 (s, 1H), 85.17 (bs, 1H), 3.73 (s, 3H), 2.8 (m, 2H), 2.1 (bd, 1H), 1.75 (m, 1H), 1.6 (m, 1H), 1.3 (m, 18H), 0.8 (t, 3H, J=7.5 Hz).

$^{13}$C NMR (CDCl$_3$): 175.7, 170.9, 166.8, 118.6, 99.1, 52.2, 43.6, 32.6, 31.9, 29.6, 29.5, 29.3, 29.1, 27, 22.6, 14.1.

MS m/e: Exact mass calculated for C$_{19}$H$_{32}$O$_5$(M+)340.2250, found 340.2239.

EXAMPLE 7

4-(2-Carboxytridecyl)-2-trimethylsilylfuran

A solution of potassium hydroxide (18 mg, 0.323 mmole), in 95% methanol (0.25 ml) was added to a 0° C. solution of 4-(2-carbomethoxytridecyl)-5-hydroxy-2(5H)-furanone (82 mg, 0.215 mmole) in 95% methanol (0.25 ml). The solution was stirred at room temperature for about 5 days. After solvent removal, the material was treated with water, acidified and extracted with ethyl acetate. The organic portions were dried over MgSO$_4$, filtered and concentrated. The residue, after solvent removal, was purified by preparative TLC (20×20 cm, 1000μ silica plate; developed with 30% ethyl acetate/hexane). The title compound was obtained as a light yellow oil.

¹H NMR (CDCl₃): 7.42 (s, 1H), 6.47 (s, 1H). 2.76 (dd, 1H, J=6.2 Hz, J=10 Hz), 2.57 (m, 2H), 1.53 (m, 2H), 1.18 (m, 18H), 0.88 (t, 3H, J=6.3 Hz), 0.23 (s, 9H).

¹³C NMR (CDCl₃): 182.3, 160.7, 143.8, 121.9, 121.0. 46.3, 31.9, 31.8. 29.6. 29.4, 29.3, 27.1, 26.9, 22.7, 14.1, −1.7.

MS m/e: Exact mass calculated for $C_{21}H_{38}O_3Si(M^+)$ 366.2590, found 366.2610.

4-(2-Carboxytridecyl)-5-hydroxy-2(5H)-furanone

A mixture of 4-(2-carboxytridecyl)-2-trimethylsilylfuran (46.3 mg, 0.126 mmol) and Rose Bengal (5 mg) in acetone (10 ml) was exposed to singlet oxygen at −78° for 2 hours. The residue, after solvent removal, was purified by preparative TLC (20×20 cm, 500μ silica plate; developed with 10% MeOH/CHCl₃ containing a few drops of acetic acid). The title compound was obtained as a colorless solid.

¹H NMR (CDCl₃): 7.0 (br, 2H), 6.03 (s, 1H), 5.9 (s, 1H), 2.75 (bm, 2H), 2.55 (bm, 2H), 1.6 (m, 2H), 1.25 (m, 18H), 0.88 (t, 3H, J=6.0 Hz).

¹³C NMR (CDCl₃): 179.6, 172.3, 167.5, 118.5, 99.7, 76.5, 43.6, 43.5, 32.6, 31.9, 30.0, 29.9. 29.9, 29.6, 29.4, 29.3, 29.1, 28.7, 27.0, 26.9, 22.7. 14.1.

MS m/e: exact mass calculated for $C_{18}H_{30}O_5(M^+)$: 326.2093, found 326.2090.

EXAMPLE 8

5-Trimethylsilyl-3-furaldehyde is treated with carbon tetrabromide and triphenylphosphine in dichloromethane at 0° to give 3-(2,2-dibromoethenyl)-5-trimethylsilylfuran. Treating with n-butyl lithium and a protected iodoalcohol I(CH₂)₈—OSI(CH₃)₂t-Bu, which is 8-iodo-0-t-butyldimethylsilyloctan-1-ol, and hexamethylphosphoramide gives 3-[t-Bu(CH₃)₂SiO—(CH₂)₈C≡C]-5-trimethylsilylfuran which is hydrogenated and treated with acetic acid to give 3-(10-hydroxydecyl)-5-trimethylsilylfuran.

Treating the above prepared 3-(10-hydroxydecyl) compound with acetic anhydride gives the 3-(10-acetoxydecyl) compound. A mixture of this compound and Rose Bengal in tetrahydrofuran is exposed to singlet oxygen at −78° for 2 hours to give 4-(10-acetoxydecyl)-5-hydroxy-2(5H)-furanone.

EXAMPLE 9

Treating 3-(10-hydroxydecyl)-5-trimethylsilylfuran with 2-chloro-2-oxo-1,3,2-dioxaphospholane and hydrolyzing gives the 3-[10-PO(OH)₂O-decyl] compound which is oxidized by procedure described in Example 8 to give 4-[10-PO(OH)₂O-decyl]-5-hydroxy-2(5H)-furanone.

EXAMPLE 10

Reacting 3-(10-hydroxydecyl)-5-trimethylsilylfuran with 4-(diethylamino)butyric acid hydrochloride in the presence of 1,3-dicyclohexylcarbodiimide and 4-dimethylaminopyridine and oxidizing gives 4-(10-diethylaminobutyryloxydecyl)-5-hydroxy-2(5H)-furanone.

EXAMPLE 11

3-(10-Hydroxydecyl)-5-trimethylsilylfuran is oxidized by Jones reagent (chromic acid) to give 3-(10-carboxydecyl)-5-trimethylsilylfuran. A mixture of this compound and Rose Bengal in tetrahydrofuran is exposed to singlet oxygen at −78° to give 4-(10-carboxydecyl)-5-hydroxy-2(5H)-furanone.

EXAMPLE 12

(E)(Z)-Methyl 3-(2-triethylsilyl-4-furyl)propen-2-oate)

A mixture of methyl(triphenylphosphoranylidene) acetate (4.77 g, 14.3 mmol) and 5-triethylsilyl-3-furaldehyde (2 0 g, 9.5 mmol) in tetrahydrofuran (30 ml) was refluxed under argon for 2 days. The reaction mixture was evaporated with a minimum amount of silica and the residue was chromatographed on a silica column using 2.5% ethyl ether/hexane to give a mixture of (E),(Z)-methyl 3-(2-triethylsilyl-4-furyl)propen-2-oate. (E)-isomer, $R_f$ 0.19 (5% ethyl ether/hexane) and (Z)-isomer, $R_f$ 0.38 (5% ethyl ether/hexane).

¹H NMR (CDCl₃) (E)-isomer: 0.78 (q, 6H, J=8.0 Hz), 0.99 (t, 9H, J=8.0 Hz), 3.78 (s, 3H), 6.15 (d, 1H, J=15.7 Hz), 6.79 (s, 1H), 7.61 (d, 1H, J=15.7 Hz) and 7.84 (s, 1H). (Z)-isomer: 0.79 (q, 6H, J=8.0 Hz), 0.99 (t, 9H, J=8.0 Hz), 3.75 (s, 3H), 5.77 (d, 1H, J=12.6 Hz), 6.74 (d, 1H, J=12.6 Hz), 7.13 (s, 1H) and 8.35 (s, 1H).

LRMS (m/e, % abundance) 266 (M⁺, 31), 238 (19), 237 (100), 209 (24), 117 (37), 89 (44) and 87 (11).

Methyl 3-(2-triethylsilyl-4-furyl)propionate

A solution of (E), (Z)-methyl 3-(2-triethylsilyl-4-furyl)propen-2-oate (1.83 g, 6.88 mmol) in ethyl acetate (10 ml) was hydrogenated over platinum (IV) oxide (ca 15 mg) at room temperature for 16 hours. The mixture was filtered through celite and the filtrate on evaporation gave oil, which was purified by a silica column using 5% ethyl ether/hexane to give the titled ester.

¹H NMR (CDCl₃): 0.72 (q, 6H, J=8.0 Hz), 0.79 (t, 9H, J=8.0 Hz), 2.57 (t, 2H, J=7.7 Hz), 2.76 (t, 2H, J=7.7 Hz), 3.68 (s, 3H), 6.50 (s, 1H) and 7.44 (s, 1H).

3-(2-Triethylsilyl-4-furyl)propan-1-ol

Lithium aluminium hydride (a 1M solution in tetrahydrofuran; 5.17 ml, 5.17 mmol) was added dropwise to a solution of methyl 3-(2-triethylsilyl-4-furyl)propionate (1.38 g, 5.17 mmol) in tetrahydrofuran (5 ml) at 0° under argon. After 20 minutes, the mixture was quenched with water and extracted with ethyl acetate. Evaporation of the dried (magnesium sulfate) extracts gave the desired alcohol, which was used directly in the next step.

¹H NMR (CDCl₃): 0.76 (q, 6H, J=8.0 Hz), 0.98 (t, 9H, J=8.0 Hz), 1.84 (m, 2H), 2.52 (t, 2H, J=7.4 Hz), 3.69 (t, 2H, 6.5 Hz), 6.52 (s, 1H) and 7.43 (s, 1H).

3-(2-Triethylsilyl-4-furyl)-1-propanol

A mixture of dimethyl sulfoxide (0.9 ml) and dichloromethane (9 ml) was added to a solution of oxalyl chloride (0.64 ml, 7.39 mmol) at −78° under argon. After 5 minutes, a solution of 3-(2-triethylsilyl-4-furyl)-propan-1-ol (1.27 g, 5.28 mmol) in dichloromethane (9.0 ml) was added dropwise and after 20 minutes, triethylamine (2.9 ml, 21.1 mmol) was added. Stirring was continued at −78° C. for 40 minutes and at room temperature for 3 hours. The mixture was quenched with water and was extracted thoroughly with ethyl ether. Evaporation of the dried (magnesium sulfate) extracts gave an oil, which was purified by a silica column to give the titled aldehyde.

¹H NMR (CDCl₃): 0.75 (q, 6H, J=7.3 Hz), 0.97 (t, 9H, J=7.3 Hz), 2.73 (m, 4H), 6.49 (s, 1H), 7.43 (s, 1H) and 9.80 (s, 1H).

¹³C NMR (CDCl₃): 2.9, 6.9, 17.1, 43.9, 121.9, 123.2, 143.5, 159.3 and 202.1.

4-(4,4-Dibromo-3-butenyl)-2-triethylsilylfuran 3-(2-triethylsilyl-4-furyl)-1-propanal (500 mg, 2.09 mmol) was added to a mixture of carbon tetrabromide (868 mg, 2.62 mmol) and triphenylphosphine (1.27 g, 5.25 mmol) in dichloromethane at 0° under argon. After 4 hours, the mixture was diluted with pentane and filtered. Evaporation of the filtrate gave a residue, which was purified by a silica column using hexane to give the titled dibromide.

$^1$H NMR (CDCl$_3$): 0.76 (q, 6H, J=8.0 Hz), 0.98 (t, 9H, J=8.0 Hz), 2.36 (dt, 2H, J=7.5 Hz), 2.55 (t, 2H, J=7.6 Hz), 6.41 (t, 1H, J=7.0 Hz), 6.50 (s, 1H) and 7.43 (s, 1H).

$^{13}$C NMR (CDCl$_3$): 3.2, 7.3, 14.1, 19.9, 22.7, 24.2, 25.2, 29.4, 29.5, 29.6, 31.6, 31.9, 38.1, 62.7, 81.9, 84.8, 121.9, 123.3, 143.3 and 158.5.

HRMS exact mass calculated for C$_{26}$H$_{46}$O$_2$Si (M+) 418.3267, found 418.3258.

4-(5-Hydroxy-3-hexadecynyl)-2-triethylsilylfuran n-Butyl lithium (a 2.5M solution in tetrahydrofuran; 0.42 ml, 1.04 mmol) was added dropwise to a solution of 4-(4,4-dibromo-3-butenyl)-2-triethylsilylfuran (200 mg, 0.51 mmol) in tetrahydrofuran (8 ml) at −78° under argon. After 2 hours, a solution of 1-dodecanal (102 mg, 0.56 mmol) in tetrahydrofuran (1 ml) was added. Stirring was continued for 14 hours, while the cooling bath attained room temperature. The mixture was quenched with water and was extracted with ethyl ether. Evaporation of the dried (magnesium sulfate) extracts gave a residue, which was purified by a silica column with 15% ethyl ether/hexane to give the titled alcohol.

$^1$H NMR (CDCl$_3$): 0.76 (q, 6H, J=8.0 Hz), 0.88 (t, 3H, J=5.3 Hz), 0.95 (t, 9H, J=8.0 Hz), 1.26 (m, 18H), 1.60 (m, 2H), 2.45 (t, 2H, J=7.4 Hz), 2.64 (t, 2H, J=7.4 Hz), 4.34 (dd, 1H, J=6.4 Hz, 5.5 Hz), 6.55 (s, 1H) and 7.48 (s, 1H).

4-(5-Oxo-3-hexadecynyl)-2-triethylsilylfuran

Jones reagent (a 2.6M solution in sulfuric acid, 0.13 ml, 0.36 mmol) was added dropwise to a solution of 4-(5-hydroxy-3-hexadecynyl)-2-triethylsilylfuran (136.4 mg, 0.33 mmol) in acetone (5 ml) at 0°. After 20 minutes, the excess Jones reagent was destroyed with ethanol (Ca 1 ml) and the mixture was diluted with water. The organic phase was separated, dried (magnesium sulfate) and evaporated down to give an oil, which was purified by preparative silica plates to give the titled ketone.

$^1$H NMR (CDCl$_3$): 0.76 (q, 6H, J=8.0 Hz), 0.88 (t, 3H, J=7.0 Hz), 0.98 (t, 9H, J=8.0 Hz), 1.25 (m, 16H), 1.60 (m, 2H), 2.50 (t, 2H, J=7.5 Hz), 2.60 (t, 2H, J=6.8 Hz), 2.71 (t, 2H, J=6.8 Hz), 6.54 (s, 1H) and 7.50 (s, 1H).

$^{13}$C NMR (CDCl$_3$): 3.2, 7.3, 14.1, 20.2, 22.7, 23.3, 24.0, 28.9, 29.3, 29.4, 29.6, 31.9, 45.5, 81.2, 93.1, 121.6, 122.6, 143.4, 159.0 and 188.4.

HRMS exact mass calculated for C$_{26}$H$_{44}$O$_2$Si (M+) 416.3105, found 416.3092.

4-(5-Oxo-3-hexadecynyl)-5-hydroxy-2(5H)-furanone

A mixture of 4-(5-oxo-3-hexadecynyl)-2-triethylsilylfuran (74.4 mg, 0.18 mmol), water (a few drops) and Rose Bengal (5 mg) in tetrahydrofuran (7 ml) was exposed to singlet oxygen at 0° for 1 hour. The residue, after solvent removal, was purified by preparative silica plates (developed with 60% ethyl ether/hexane) to give the titled furanone.

$^1$H NMR (CDCl$_3$): 0.88 (t, 3H, J=6.9 Hz), 1.26 (m, 16H), 1.65 (m, 2H), 2.53 (t, 2H, J=7.4 Hz), 2.75 (m, 4H), 4.35 (brs, 1H), 6.00 (s, 1H) and 6.08 (d, 1H, J=7.4 Hz).

$^{13}$C NMR (CDCl$_3$): 13.8, 16.4, 22.4, 23.7, 25.7, 28.7, 29.1, 29.2, 29.4, 31.7, 45.3, 81.6, 91.3, 99.1, 118.7, 166.8, 171.5 and 189.3.

HRMS exact mass calculated for C$_{20}$H$_{31}$O$_4$ (M+H)+ 335.2222, found 335.2226.

EXAMPLE 13

3-(2-Trimethylsilyl-4-furyl)propan-1-al is treated with (triphenylphosphoranylidene) acetaldehyde in tetrahydrofuran to give 5-(2-trimethylsilyl-4-furyl)pent-2-en-1-al which is hydrogenated in the presence of a palladium catalyst to give 5-(2-trimethylsilyl-4-furyl)-pentan-1-al. Treating this intermediate with C$_9$H$_{19}$COCH$_2$PO(OCH$_3$)$_2$ and sodium hydride in tetrahydrofuran gives 3-(7-oxo-5-hexadecenyl)-5-trimethylsilylfuran and oxidizing gives 4-(7-oxo-5-hexadecenyl)-5-hydroxy-2(5H)-furanone.

EXAMPLE 14

Hydrogenating 3-(7-oxo-5-hexadecenyl)-5-trimethylsilylfuran using platinum oxide as catalyst by the procedure of Example 4 and oxidizing gives 4-(7-oxohexadecyl)-5-hydroxy-2(5H)-furanone.

EXAMPLE 15

3-(2-Trimethylsilyl-4-furyl)propan-1-al is reacted with dioctylmalonate in tetrahydrofuran in the presence of acetic acid and piperidine to give 3-[4,4-di (carbooctanoxy)-3-butenyl]- 5-trimethylsilylfuran which is treated with cold aqueous potassium hydroxide to give 3-(4-carboxy-4-carbooctanoxy-3-butenyl)-5-trimethylsilylfuran.

A mixture of the above prepared furan compound and Rose Bengal in tetrahydrofuran is exposed to singlet oxygen at −78° for 2 hours to give 4-(4-carboxy-4-carbooctanoxy-3-butenyl)-5-hydroxy-2(5H)-furanone.

EXAMPLE 16

3-(4-Carboxy-4-carbooctanoxy-3-butenyl)-5-trimethylsilylfuran is reacted with ethanol in the presence of 1,3-dicyclohexylcarbodiimide and 4-dimethylaminopyridine to give 3-(4-carboethoxy-4-carbooctanoxy-3-butenyl)-5-trimethylsilylfuran. Oxidizing this intermediate gives 4-(4-carboethoxy-4-carbooctanoxy-3-butenyl)-5-hydroxy-2(5H)-furanone.

EXAMPLE 17

4-[4-Carboethoxy-(E)-3-tetradecenyl]-5-hydroxy-2(5H)-furanone.

A stirred solution of (E)-ethyl 2-decyl-5-(2-trimethylsilyl-4-furyl)penten-2-oate (0.100 g, 0.246 mmol) and Rose Bengal in acetone (2 ml) was flushed with oxygen and cooled to −78°. The solution was subsequently irradiated with a 150 watt flood lamp while under constant positive pressure of oxygen until no starting material was visible by TLC. The solution was warmed to room temperature and concentrated to give a pink oil. Purification by flash chromatography (silica, 40% ethyl acetate/hexane) gave the desired hydroxybutenolide.

IR (CHCl$_3$): 3400 (broad), 2930, 1755, 1700 cm$^{-1}$.

$^1$H NMR (CDCl$_3$): 6.04 (s, 1H); 5.84 (s, 1H); 5.76 to 5.82 (m, 2H); 4.20 (q, J=7.0 Hz, 2H); 2.42 to 2.82 (m,

4H); 2.24 (t, 2H, J=7.3 Hz); 1.15 to 1.45 (m, 19H); 0.88 (t, 3H, J=6.6 Hz).

$^{13}$C NMR (CDCl$_3$): 171.0, 168.3, 167.6, 138.2, 134.8, 118.6, 99.4, 60.7, 34.4, 31.9, multiple peaks from 29.1 to 29.6, 27.1. 26.6, 22.7, 14.1.

MS m/e: Calculated for C$_{21}$H$_{34}$O$_5$ (M+): 366.2406, found 366.2424.

EXAMPLE 18

4-[4-Carboethoxy-(Z)-3-tetradecenyl]-5-hydroxy-2(5H)-furanone

A stirred solution of (Z)-ethyl 2-decyl-5-(2-trimethylsilyl-4-furyl)penten-2-oate (0.164 g, 0.404 mmol) and Rose Bengal in acetone (2 ml) was flushed with oxygen and cooled to −78°. The solution was subsequently irradiated with a 150 watt flood lamp while under constant, positive pressure of oxygen until no starting material was visible by TLC. The solution was warmed to room temperature and concentrated to give a pink oil. Purification by flash chromatography (silica, 40% ethyl acetate/petroleum ether) gave the desired hydroxybutenolide.

IR (CHCl$_3$): 3300 (broad), 2920, 1750, 1690 cm$^{-1}$.

$^1$H NMR (CDCl$_3$): 6.68 (t, J=6.6 Hz, 1H); 6.01 (brs, 1H); 6.05 (brs, 1H); 5.87 (s, 1H); 4.19 (q, 2H, J=7.1 Hz); 2.45 to 2.71 (m, 4H); 2.30 (t, 2H, J=7.3 Hz); 1.15 to 1.45 (m, 19H); 0.88 (t, 3H, J=6.6 Hz).

+$^{13}$C NMR (CDCl$_3$): 171.6, 168.6, 168.0, 139.3, 134.3, 117.6, 99.3, 60.7, 31.8, multiple peaks between 29.1 and 29.5, 26.8, 26.7, 25.3, 22.6, 14.1, 14.0.

MS m/e: Calculated for C$_{21}$H$_{34}$O$_5$ (M+): 366.2406, found 366.2408.

EXAMPLE 19

4[2-Carbo(3-(2,4,5-trifluorophenyl)propoxy)ethyl]-5-hydroxy-2(5H)-furanone-3-(2,4,5-trifluorophenyl) prop-2-yn-1-ol A mixture of 2,4,5-trifluorobromobenzene(1.04 g, 4.9 mmol), bis(triphenylphosphine)palladium (II) chloride (5 mg), copper (I) iodide (5 mg) in triethylamine (20 ml) was deaerated with argon for 5 min. After propargyl alcohol (0.32 ml, 5.4 mmol) was added, the solution was rapidly heated to reflux under argon and conditions maintained for 16 hours. On cooling, the mixture was poured into ice cold dilute hydrochloric acid and extracted thoroughly with ether. Evaporation of the dried (magnesium sulfate) extracts gave an oil, which was flash chromatographed on silica using 30% ether/hexane. Fractions with R$_f$ of about 0.24 on evaporation gave the title alcohol as a light tan oil.

$^1$H NMR(CDCl$_3$): 1.90 (br, 1H), 4.54 (p, 2H), 6.90 (m, 1H) and 7.25 (m, 1H).

MS m/e (% abundance): 186 (M+, 77), 169 (57), 158 (100), 137 (73), 119 (14) and 105 (14).

3-(2,4,5-Trifluorophenyl)-propan-1-ol

A solution of 3-(2,4,5-trifluorophenyl)prop-2-yn-1-ol (90 mg, 0.48 mmol) in diethyl ether (10 ml) was hydrogenated over 10% palladium on carbon at room temperature for 15 hours. The mixture was filtered through celite and the filtrate on evaporation gave an oil, which was flash chromatographed on silica using 10% ethyl ether/hexane. Fractions with R$_f$ of about 0.16 on evaporation gave the title alcohol as a colorless oil.

$^1$H NMR(CDCl$_3$): 1.45 (br, 1H), 1.87 (p, 2H, J=6.4 Hz), 2.73 (t, 2H, J=7.8 Hz). 3.71 (t, 2H, J=6.3 Hz), 6.90 (m, 1H) and 7.05 (m, 1H).

MS m/e (% abundance): 191 ((M+H)+, 13), 190 (M+13), 190 (M+, 14), 189 (24), 173 (100), 172 (38), 150 (11) and 145 (39).

3-(5-Trimethylsilyl-3-furyl)propionic acid

A solution of potassium hydroxide (446 mg, 7.96 mmol) in 95% ethanol/water (4 ml) was added to a solution of methyl 3-(5-trimethylsilyl-3-furyl)propionate(1.2 g, 5.3 mmol), prepared as in Example 2, in 95% ethanol/water (4ml) at 0°. After stirring at 0° for 5 hours and at room temperature for 5 hours, most of the solvent was evaporated. The residue was dissolved in ethyl acetate (15 ml), acidified with hydrochloric acid and the mixture then extracted thoroughly with ethyl acetate. Evaporation of the dried (magnesium sulfate) extracts gave an oil, which on crystallization from hexane (−78°) gave the title acid as colorless needles, mp ca. 25°.

$^1$H NMR (CDCl$_3$): 0.29 (s, 9H), 2.66 (t, 2H, J=6.8 Hz), 2.78 (t, 2H, J=6.8 Hz), 6.54 (s, 1H) and 7.49 (s, 1H).

MS m/e (% abundance): 212 (M+, 49), 197 (30), 156 (13), 155 (100), 75 (74) and 73 (34).

3-(2,4,5-Trifluorophenyl)propyl-3-(5-trimethylsilyl-3-furyl)proprionate

A mixture of 3-(5-trimethylsilyl-3-furyl)propionic acid (61.3 mg, 0.29 mmol), 3-(2,4,5-trifluorophenyl)propan-1-ol (55 mg, 0.29 mmol), 1,3-dicyclohexylcarbodiimide (66 mg, 0.32 mmol) and 4-dimethylaminopyridine (10 mg) in dichloromethane (3 ml) was stirred at room temperature overnight (17 hours). Most of the solvent was evaporated and the residue was purified by preparative TLC (20×20 cm, 1000μ silica plate; developed with 10% ethyl ether/hexane). The title ester was obtained as a colorless oil.

$^1$H NMR(CDCl$_3$): 0.26 (s, 9H), 1.93 (p, 2H, J=6.6 Hz), 2.60 (t, 2H, J=7.0 Hz), 2.63 (t, 2H, J=9.9 Hz), 2.79 (t, 2H, J=7.5 Hz), 4.12 (t, 2H, J=6.3 Hz), 6.53 (s, 1H), 6.85-7.05 (m, 2H) and 7.46 (s,1H)

4-[2-Carbo-(3-(2,4,5-trifluorophenyl)propoxy)ethyl]-5-hydroxy-2(5H)-furanone

A mixture of 3-(2,4,5-trifluorophenyl)propyl-3-(5-trimethylsilyl-3-furyl)-ropionate (47.4 mg, 0.12 mmol) and Rose Bengal (5 mg) in tetrahydrofuran (6 ml) was exposed to singlet oxygen at −78° for 2 hours. The residue, after solvent removal, was purified by preparative TLC (20×20 cm, 1000μ silica plate; developed with 60% ethyl ether/hexane). The title furanone was obtained as a pale yellow oil.

$^1$H NMR (CDCl$_3$): 1.99 (p, 2H, J=7.9 Hz), 2.65–2.80 (m, 6H), 4.15 (t, 2H, J=6.4 Hz), 4.85 (br, 1H), 5.92 (s, 1H), 6.06 (s, 1H) and 6.86–7.10 (m, 2H).

$^{13}$C NMR (CDCl$_3$): 22.3, 24.9, 28.6, 31.5, 64.2, 98.9, 105.1, 105.4, 105.5, 105.7, 117.7, 117.8, 117.9, 118.0, 118.3, 118.4, 167.1, 170.2 and 172.4.

MS m/e: Exact mass calculated for C$_{16}$H$_{16}$F$_3$O$_5$ (M+H)+ 345.0940, found 345.0949.

EXAMPLE 20

3-[2-N-(2-phenylethyl)amidoethyl)]-5-trimethylsilylfuran

A mixture of 3-(5-trimethylsilyl-3-furyl)propionic acid (150 mg), 0.71 mmol), 2-phenylethylamine (98 μl, 0.78 mmol), 1,3-dicyclohexylcarbodiimide (160 mg, 0.78 mmol) and 4-dimethylaminopyridine (10 mg) in dichloromethane (3 ml) was stirred at room temperature overnight. Most of the solvent was evaporated and the residue was purified by preparative TLC (20×20 cm, 1000μ silica plate; developed with 60% ethyl ether/hexane). The title amide was obtained as a colorless oil.

$^1$H NMR (CDCl$_3$): 0.27 (s, 9H), 2.39 (t, 2H, J=7.2 Hz), 2.81 (2t, 2H, J=7.7 Hz, 7.0 Hz), 3.53 (2t, 2H, J=6.3 Hz), 5.45 (br, 1H), 6.52 (s, 1H), 7.15–7.40 (m, 5H) and 7.43 (s, 1H).

4-[2-(N-(2-Phenylethyl)amidoethyl)]-5-hydroxy-2(5H)-furanone

A mixture of 3-[2-(N-(2-phenylethyl) -amidoethyl)]-5-trimethylsilylfuran (90.6 mg, 0.29 mmol) and Rose Bengal (5 ml) in tetrahydrofuran (7 ml) was exposed to singlet oxygen at −78° for 2 hours. The residue, after solvent removal, was purified by preparative TLC (20×20 cm, 1000μ silica plate, developed with ethyl acetate). The title furanone was obtained as a very pale yellow oil.

$^1$H NMR (CDCl$_3$): 2.45–2.75 (m, 4H), 2.84 (t, 2H, J=6.8 Hz), 3.54 (dd, 2H, J=6.7 Hz, 12.9 Hz), 5.84 (brs, 1H), 6.0 (brs, 1H), 6.76 (brs, 1H) and 7.15–7.45 (m, 5H).

$^{13}$C NMR (CDCl$_3$): 23.2, 33.2, 35.3, 40.9, 99.7, 118.0, 126.6, 128.6, 128.7, 128.9, 138.5, 168.6, 171.5 and 171.9.

MS: Exact mass calculated for C$_{15}$H$_{18}$NO$_4$ (M+NH$_4$)$^+$: 276.1236, found 276.1246.

EXAMPLE 21

3-[2-(M-methyl-N-(2-phenyethyl)amidoethyl)]-5-trimethylsilylfuran

A mixture of 3-(5-trimethylsilyl-3-furyl)propionic acid (207.3 mg, 0.98 mmol), N-methyl-2-phenylethylamine (0.16 ml, 0.11 mmol), 1,3-dicyclohexylcarbodiimide (221 mg, 0.12 mmol) and 4-dimethylaminopyridine in dichloromethane (3 ml) was stirred at room temperature overnight (14 hours). Most of the solvent was evaporated and the residue was purified by preparative TLC (20×20 cm), 1000μ silica plate; developed with 60% ethyl ether/hexane). The title amide was obtained as a pale yellow oil.

$^1$H NMR (CDCl$_3$) (mixture of 2 isomers): 0.29 (s, 18H), 2.31 (t, 2H, J=8.3 Hz), 2.57 (s, 2H, J=8.2 Hz), 2.68 (t, 2H, J=7.5 Hz), 2.85 (m, 2H), 2.90 (s, 3H), 3.01 (s, 3H), 3.54 (t, 2H, J=7.3 Hz), 3.65 (s, 2H, J=7.7 Hz), 6.46 (s, 1H), 6.57 (s, 1H), 7.15–7.36 (m, 10), 7.41 (s, 1H) and 7,49 (s, 1H).

MS m/e (% abundance): 329 (m+, 50), 314 (11), 239 (14), 238 (79), 195 (40), 167 (27), 153 (51), 105 (24), 91 (28), 77 (10), 73 (100) and 59 (12).

4-[2-(N-methyl-N-(2-phenylethyl)amidoethyl)]-5-hydroxy-2-(5H)-furanone

A mixture of 3-[2-(N-methyl-N-(2-phenylethyl)amidoethyl)]-5-trimethyl-silylfuran (119.8 mg) and Rose Bengal (5 ml) in tetrahydrofuran (7 ml) was exposed to singlet oxygen at −78° for 2 hours. The residue, after solvent removal, was purified by preparative TLC (20×20 cm, 1000μ silica plate; developed with ethyl acetate). The title furanone was obtained as a pale yellow oil.

$^1$H NMR (CDCl$_3$) (mixture of diasteriomers): 2.30 (m, 2H), 2.65 (m, 2H), 2.85 (m, 2H), 2.92 (s, 3H), 2.99 (s, 3H), 3.55 (m, 2H), 5.48 (s, 1H), 5.79 (s, 1H), 5.92 (brs, 1H), 6.03 (brs, 1H) and 7.10–7.40 (m, 10H)

$^{13}$C NMR (CDCl$_3$): 22.0, 30.7, 31.5, 33.4, 33.5, 34.1, 35.9, 49.9. 51.3, 99.7, 99.8, 117.6, 117.7, 126.4, 127.0, 128.4, 128.6, 128.8, 137.8, 138.4, 168.8, 168.9, 171.1 and 171.4.

MS: Exact mass calculated for C$_{16}$H$_{19}$NO$_4$(M$^+$) 289.1314, found 289.1320.

EXAMPLE 22

3-[2-2-Pyridyl)ethoxycarbonylethyl]-5-trimethylsilylfuran

A mixture of 3-(5-trimethylsilyl-3-furyl)propionic acid (205.0 mg, 0.97 mmol), 2-(2-hydroxyethyl)pyridine (0.12 ml, 0.11 mmol), 1,3-dicyclohexylcarbodiimide (220 mg, 0.11 mmol) and 4-dimethylaminopyridine (10 mg) in dichloromethane (4 ml) was stirred at room temperature overnight (15h). The residue, after solvent removal, was purified by preparative TLC (20×20 cm, 1000μ silica plate; developed with 60% ethyl ether/hexane). The title ester was obtained as a pale yellow oil.

$^1$H NMR (CDCl$_3$) 0.27 (s, 9H), 2.56 (t, 2H, J=7.6 Hz), 2.75 (t, 2H, J=7.7 Hz), 3.14 (t, 2H, J=6.8 Hz), 4.52 (t, 2H, J=6.8 Hz), 6.50 (s, 1H), 7.19 (m, 2H), 7.41 (s, 1H), 7.64 (t, 1H, J=7.7 Hz) and 8.60 (m, 1H).

MS m/e (% abundance) 317 (M$^+$, 25), 302 (12), 195 (18), 194 (92), 166 (35), 151 (26), 124 (11), 122 (25), 107 (61), 106 (100), 93 (23) and 73 (48).

4-[2-(2-Pyridyl)ethoxycarbonylethyl]-5-hydroxy-2(5H)-furanone

A mixture of 3-[2-(2-pyridyl)ethoxycarbonyl ethyl]-5-trimethylsilylfuran (164.4 mg, 0.52 mmol) and Rose Bengal (5 mg) intetrahydrofuran (7 ml) was exposed to singlet oxygen at −78° for 2 hours. The residue, after solvent removal, was purified by preparative TLC (20×20 cm, 1000μ silica plate; developed with ethyl acetate). The title furanone was obtained as a colorless solid, mp 125°–6°.

$^1$H NMR (CDCl$_3$): 2.70 (m, 3H), 2.95 (m, 1H), 3.15 (m, 2H), 4.45 (m, 1H), 4.55 (m, 1H), 5.80 (s, 1H), 6.06 (s, 1H), 7.25 (m, 2H), 7.75 (dt, 1H, J=7.7 Hz, 1.8 Hz), 8.15 (br, 1H) and 8.53 (dt, 1H, J=4.4 Hz, 1.0 Hz).

$^{13}$C NMR (CDCl$_3$): 22.7, 31.4, 37.0, 64.6, 99.4, 117.6, 122.5, 123.8, 137.7, 148.5, 158.0, 167.9 and 171.7.

MS m/e: Exact mass calculated for C$_{14}$H$_{16}$NO$_5$ (M+H)$^+$ 278.1028, from 278.1039.

EXAMPLE 23

4-[2-(2-Naphthyl)ethoxycarbonyl)ethyl)-5-hydroxy-2-(5H)-furanone

Using 2-(2-hydroxyethyl)naphthalene in place of 2-(2-hydroxyethyl)pyridine in the procedure of Example 22 gives the title compound.

EXAMPLE 24

Dimethyl-2-oxotridecylohosphonate

To a stirred solution of methyl laurate (1.5 g, 7.0 mmol) in tetrahydrofuran (120 ml) at −78° was added the lithium salt of dimethylmethylphosphonate (0.901 g, 7.26 mmol; generated with n-butyl lithium (5.29 ml of a 1.39M solution in hexane). The stirring mixture was warmed to room temperature over four hours and partitioned between ethyl ether and 5% aqueous ammonium chloride solution. The organic portion was washed with 5% sodium bicarbonate, water, saturated sodium chloride solution, dried over magnesium sulfate, filtered and concentrated to give a colorless oil. Purification by flash chromatography (silica, 80% to 90% ethyl acetate/hexane) gave the desired phosphonate ester.

IR (CHCl$_3$): 2920, 2850, 1710, 1250 cm$^{-1}$.

$^1$H NMR (CDCl$_3$): 3.81 (s, 3H), 3.77 (s, 3H), 3.09 (d, 2H, J=22.7 Hz), 2.61 (t, 2H, J=7.3 Hz), 1.51-1.62 (m, 2H), 1.20-1.35 (m, 16H), 0.88 (t, 3H, J=6.7 Hz).

$^{13}$C NMR (CDCl$_3$): 201.9, 52.9, 52.8, 44.1, 42.0, 40.2, 31.8, 29.5, 29.2, 28.9, 28.8, 23.3, 22.5, 14.0.

HRMS m/e: Calculated for C$_{15}$H$_{31}$O$_4$P(M+) 306.1960, found 306.1963.

4-(3-Oxo-1-tetradecenyl)-2-trimethylsilylfuran

A solution of dimethyl-2-oxotridecylphosphonate (984 mg, 3.21 mmol) in tetrahydrofuran (25 ml) was added dropwise to a suspension of sodium hydride (128 mg; a 60% suspension in mineral oil) in tetrahydrofuran (5 ml) at 0° under argon. After 1.5 hours at room temperature, the mixture was cooled to 0° and a solution of 5-trimethylsilyl-3-furaldehyde (450 mg, 2.68 mmol) in tetrahydrofuran (15 ml) was added. Stirring was continued for 14 hours, while the cooling bath attained room temperature. The mixture was quenched with 5% ammonium chloride and washed with 5% sodium bicarbonate and water. Evaporation of the dried (magnesium sulfate) organic phase gave a residue, which was purified by a silica column using 5% ethyl acetate/hexane to give the titled ketone.

IR (CHCl$_3$): 2920 and 1610.

$^1$H NMR (CDCl$_3$): 0.25 (s, 9H), 0.84 (t, 3H, J=6.8 Hz), 1.26 (m, 16H), 1.63 (m, 2H), 2.56 (t, 2H, J=7.5 Hz), 6.44 (d, 1H, J=15.9 Hz), 6.77 (s, 1H), 7.45 (d, 1H, J=16.0 Hz) and 7.82 (s, 1H).

$^{13}$C NMR (CDCl$_3$): −2.2, 13.8, 22.4, 24.3, 29.1, 29.2, 29.3, 29.4, 31.7, 40.7, 117.0, 123.0, 126.0, 132.6, 149.3, 163.4 and 201.0.

HRMS exact mass calculated for C$_{21}$H$_{36}$O$_2$Si (M+) 348.2485, found 348.2477.

4-(3-Oxotetradecenyl)-2-trimethylsilylfuran

A solution of 4-(3-oxo-1-tetradecenyl)-2-trimethylsilylfuran (315.0 mg, 0.90 mmol) in ethyl acetate (5 ml) was hydrogenated over platinum (IV) oxide (21 mg) at room temperature for 2 days. The mixture was filtered through celite and the filtrate was evaporated down to give an oil. Purification of this oil on a silica column using 3% ethyl ether/hexane gave the titled ketone.

IR (CHCl$_3$): 2930 and 1705.

$^1$H NMR (CDCl$_3$): 0.20 (s, 9H), 0.84 (t, 3H, J=6.8 Hz), 1.23 (m, 16H), 1.52 (m, 2H), 2.35 (t, 2H, J=7.4 Hz), 2.63 (m, 4H), 6.44 (s, 1H) and 7.36 (s, 1H).

$^{13}$C NMR (CDCl$_3$): −2.0, 13.8, 18.5, 22.4, 23.6, 29.0, 29.1, 29.2, 29.4, 31.7, 42.8, 42.9, 121.0, 124.0, 143.3, 160.9 and 210.6.

HRMS exact mass calculated for C$_{21}$H$_{38}$O$_2$Si 350.2641 (M+), found 350.2641.

4-(3-Oxotetradecanyl)-5-hydroxy-2(5H)-furanone

A mixture of 4-(3-oxo-1-tetradecanyl)-2-trimethylsilylfuran (141 mg, 0.40 mmol), water (a few drops) and Rose Bengal (5 mg) in tetrahydrofuran (10 ml) was exposed to singlet oxygen at 0° for 3 hours. The residue, after solvent removal, was purified by a silica column using 40% ethyl acetate/hexane to give the titled furanone.

IR (CHCl$_3$): 3400, 1755 and 1710.

$^1$H NMR (CDCl$_3$): 0.88 (t, 3H, J=6.8 Hz), 1.28 (m, 16H), 1.57 (m, 2H), 2.47 (t, 2H, J=7.5 Hz), 2.67 (m, 2H), 2.83 (t, 2H, J=6.8 Hz), 5.80 (s, 1H) and 6.05 (brs, 2H).

$^{13}$C NMR(CDCl$_3$): 13.7, 21.1, 22.4, 23.5, 23.6, 28.9, 29.0, 29.1, 29.2, 29.3, 31.6, 39.3, 42.6, 99.5, 117.7, 169.1, 171.8 and 210.4.

HRMS exact mass calculated for 311.2222 (M+H)+, found 311.2222.

EXAMPLE 25

5-Trimethylsilyl-3-furaldehyde is reacted with diethyl 2-oxotridecyl phosphate and n-butyl lithium and the resulting 5-trimethylsilyl-3-(3-oxo-1-tetradecenyl)-furan is hydrogenated (palladium on charcoal). The resulting 5-trimethylsilyl-3-(3-oxotetradecyl)furan is reacted with methyl magnesium chloride. Oxidizing the resulting 3-hydroxy-3-methyltetradecyl intermediate gives 4-(3-hydroxy-3-methyltetradecyl)-5-hydroxy-2(5H)-furanone.

EXAMPLE 26

Reacting 3-(2-trimethylsilyl-4-furyl)propanal with O-octyl-hydroxylamine or N-decylhydrazine and oxidizing the resulting intermediate by treating with oxygen using Rose Bengal as initiator gives:

O-octyloxime of 4-(3-oxopropyl)-5-hydroxy-2(5H)furanone and the

N-decylhydrazone of 4-(3-oxopropyl)-5-hydroxy-2(5H)-furanone.

EXAMPLE 27

2-Trimethylsilyl-4-(o-hydroxybenzoylethyl)furan is reacted with hydroxylamine to give the oxime and oxidizing by treating with oxygen and Rose Bengal gives the oxime of 4-(o-hydroxy-benzoylethyl)-5-hydroxy-2(5H) furanone.

The starting material is prepared by reacting o-hydroxybenzoic acid with benzyl bromide and then with thionyl chloride to give o-benzyloxybenzoyl chloride. Reacting this intermediate with dimethyl methylphosphonate and then with 2-trimethylsilyl-4-furaldehyde gives 2-trimethylsilyl-4-(o-benzyloxybenzoylethenyl)furan which is hydrogenated to give the 2-TMS-4-(o-hydrobenzoylethyl)furan.

EXAMPLE 28

4-(3-Hydroxy-4-hexadecynyl)-2-triethylsilylfuran n-Butyl lithium (a 2.5M solution in tetrahydrofuran; 0.58 ml, 1.44 mmol) was added dropwise to a solution of 1-tridecyne (259 mg, 1.44 mmol) in tetrahydrofuran (6 ml) at 0°. After 1 hour, a solution of (2-triethylsilyl-4-furyl)-1-propanal (312 mg, 1.31 mmol) in tetrahydrofuran (1 ml) was added. Stirring was continued for 14 hours, while the cooling bath attained room temperature. The mixture was quenched with water and was extracted with ethyl ether. Evaporation of the dried (magnesium sulfate) extracts gave an oil, which was purified by a silica column using 15% ethyl ether/hexane to give the titled alcohol.

$^1$H NMR (CDCl$_3$): 0.75 q, 6H, J=8.0 Hz), 0.98 (t, 9H, J=8.0 Hz), 1.20 (m, 16H), 1.45 (m, 2H), 1.71 (d, 1H, J=5.4 Hz), 1.95 (m, 2H), 2.21 (t, 2H, J=7.2 Hz), 2.59 (t, 2H, J=7.8 Hz), 4.37 (dd, 1H, J=5.4 Hz, 3.6 Hz), 6.52 (s, 1H) and 7.43 (s, 1H).

4-(3-Oxo-4-hexadecynyl)-2-triethylsilylfuran

Jones reagent (a 2.67M solution in sulfuric acid; 50 μl, 0.14 mmol) was added to a solution of 4-(3-hydroxy-4-hexadecynyl)-2-triethylsilylfuran (53.6 mg, 0.13 mmol) in acetone (5 ml) at 0°. After 25 minutes, the mixture was quenched with ethanol, diluted with water and was extracted with ethyl ether. Evaporation of the dried (magnesium sulfate) extracts gave an oil, which was purified by preparative silica plates to give the titled ketone.

$^1$H NMR (CDCl$_3$): 0.75 (q, 6H, J=8.0 Hz), 0.88 (t, 3H, J=6.9 Hz), 0.97 (t, 9H, J=8.0 Hz), 1.30 (m, 14H), 1.40 (m,2H), 1.60 (m, 2H), 2.36 (t, 2H, J=7.1 Hz), 2.79 (s, 4H), 6.49 (s, 1H) and 7.42 (s, 1H).

$^{13}$C NMR (CDCl$_3$): 3.2, 7.3, 14.1, 18.9, 19.2, 22.7, 27.7, 28.8, 29.0, 29.2. 29.3, 29.4, 29.6, 31.9, 45.8, 77.8, 80.7, 94.9, 121.8, 123.0. 143.2, 158.8 and 18.73.

LRMS (m/e, % abundance): 417 [(M+H)$^+$, 53], 416 (76), 388 (43), 359 (26), 289 (16), 285 (16), 276 (56), 261 (15), 250 (17), 249 (45), 247 (34), 233 (19), 222 (32), 221 (47), 216 (36), 210 (17), 209 (81), 201 (19), 195 (30), 167 (91), 165 (78), 103 (100), 95 (23), 91 (16), 87 (81).

4-(3-Oxo-4-hexadecynyl)-5-hydroxy-2(5H)-furanone

A mixture of 4-(3-oxo-4-hexadecynyl)-2-triethylsilylfuran (40 mg, 0.096 mmol), water (2 drops) and Rose Bengal (3 mg) in tetrahydrofuran (7 ml) was exposed to singlet oxygen at −78° for 1.5 hours. The residue, after solvent removal, was purified by preparative silica plates to give the titled furanone.

$^1$H NMR (CDCl$_3$): 0.88 (t, 3H, J=6.4 Hz), 1.26 m, 14H), 1.59 (m, 4H), 2.39 (t, 2H, J=7.1 Hz), 2.70 (m, 2H), 2.97 (t, 2H, J=6.4 Hz), 4.25 (brs, 1H), 5.86 (s, 1H) and 6.01 (d, 1H, J=5.3 Hz).

$^{13}$C NMR (CDCl$_3$): 14.1, 19.0, 21.4, 22.7, 27.6, 28.9, 29.3, 29.4, 29.6, 31.9, 42.3, 80.3, 96.9, 99.0, 118.2, 167.2, 170.7 and 185.7.

HRMS exact mass calculated for C$_{20}$H$_{34}$NO$_4$ (M+NH$_4$)$^+$ 352.2488, found 352.2486.

EXAMPLE 29

5-Triethylsilyl-3-furaldehyde, prepared by the alternative preparation described hereinabove using triethylsilyl chloride in place of trimethylsilyl chloride is converted to 3-(2-triethylsilyl-4-furyl)propan-1-al by the procedure of Examples 2 and 3. 3-(2-Triethylsilyl-4-furyl)propan-1-al is reacted with octyl acetate and lithium diisopropylamide and the resulting hydroxy ester is reacted with acetic anhydride to give 4-(3-acetoxy-5-carbooctanoxybutyl)-5-hydroxy-2(5H)-furanone.

EXAMPLE 30

4-(3-Acetoxy-4-Carbooctanoxy)butyl-2-triethylsilylfuran

Octyl acetate (238.0 mg, 1.38 mmol) was added to a solution of lithium diisopropylamide (1.38 mmol; prepared from 0.19 ml diisopropylamine and 1.38 mmol n-butyl lithium at −78°) in tetrahydrofuran (8 ml) at −78° under argon. After 1 hour, a solution of (2-triethylsilyl-4-furyl)-1-propanal (300 mg, 1.26 mmol) in tetrahydrofuran (2 ml), followed by acetic anhydride (0.36 ml, 3.78 mmol) after 1 hour, was added. Stirring was continued for 14 hours, while the cooling bath attained room temperature. The reaction mixture was quenched with water and was extracted with ethyl ether. Evaporation of the dried (magnesium sulfate) extracts gave an oil, which was purified by preparative silica plates to give the titled ester.

$^1$H NMR (CDCl$_3$): 0.75 (q, 6H, J=8.0 Hz), 0.86 (t, 3H, J=6.6 Hz), 0.97 (t, 9H, J=8.0 Hz), 1.25 (m, 10H), 1.61 (m, 2H), 1.85 (m, 2H), 2.03 (s, 3H), 2.44 (m, 2H), 2.58 (dd, 2H, J=9.0 Hz), 4.06 (t, 2H, J=6.8 Hz), 5.26 (m, 1H), 6.49 (s, 1H) and 7.42 (s, 1H).

$^{13}$C NMR (CDCl$_3$): 3.2, 7.3, 14.1, 20.5, 21.0, 22.6, 25.8, 28.5, 29.2, 31.8, 34.3, 39.2, 64.9, 70.2, 121.8, 123.6, 143.1, 158.7 and 170.4.

HRMS exact mass calculated for C$_{25}$H$_{45}$O$_5$Si (M$^+$) 453.3036, found 453.3024.

4-(3-Acetoxy-4-carbooctanoxy)butyl-5-hydroxy-2(5H)-furanone

A mixture of 4-(3-acetoxy-4-carbooctanoxy) butyl-2-triethylsilylfuran (120 mg, 0.27 mmol), water (a few drops) and Rose Bengal (5 mg) in tetrahydrofuran (6 ml) was exposed to singlet oxygen at 0° for 1 hour. The residue, after solvent removal, was purified by preparative silica plates to give the desired furanone.

$^1$H NMR (CDCl$_3$): 0.88 (t, 3H, J=6.4 Hz), 1.27 (m, 12H), 1.61 (m, 2H), 1.96 (m, 2H), 2.06 (s, 3H), 2.43 (m, 2H), 2.62 (ddd, 2H, J=16.6 Hz, 16.0 Hz, 6.8 Hz), 4.08 (t, 2H, J=6.8 Hz), 4.44 (brs, 1H), 5.26 (m, 1H), 5.94 (s, 1H) and 5.99 (brs, 1H).

$^{13}$C NMR (CDCl$_3$): 14.0, 15.1, 21.0, 22.6, 23.4, 23.6, 25.8, 28.4, 29.1, 30.6, 31.7, 38.8, 38.9, 65.1, 65.8, 69.3, 69.4, 69.5, 99.2, 117.6, 168.1, 168.3, 170.4, 171.0 and 171.3.

HRMS exact mass calculated for C$_{19}$H$_{31}$O$_7$ (M+H)$^+$ 371.2070, found 371.2071.

EXAMPLE 31

N-Dodecyl-3-(2-triethylsilyl-4-furyl)-1-propionamide

A mixture of 3-(2-triethylsilyl-4-furyl)-1-propanoic acid (250 mg, 1.18 mmol), dicyclohexylcarbodiimide (360 mg, 1.77 mmol), 4-dimethylaminopyridine (ca 10 mg) and 1-dodecylamine (330 mg, 1.77 mmol) in dichloromethane (5 ml) was stirred at room temperature for 2 days. The mixture was quenched with water and extracted with ethyl ether. Evaporation of the dried (magnesium sulfate) extracts gave an oil, which was purified by preparative silica plates to give the titled amide.

$^1$H NMR (CDCl$_3$): 0.64 (t, 3H, J=6.5 Hz), 1.02 (m, 18H), 1.20 (m, 2H), 2.15 (t, 2H, J=7.7 Hz), 2.53 (t, 2H, J=7.7 Hz), 2.98 (dt, 2H, J=12.9 Hz, 5.9 Hz), 5.11 (br, 1H), 6.26 (s, 1H) and 7.19 (s, 1H).

$^{13}$C NMR (CDCl$_3$): 13.8, 20.5, 22.4, 26.6, 29.1, 29.3, 29.4, 31.7, 37.3, 39.4, 120.9, 123.8, 143.4, 161.1 and 172.4.

HRMS exact mass calculated for C$_{22}$H$_{41}$NO$_2$Si (M$^+$) 379.2906, found 379.2900.

4-[2-(N-Dodecyl)amidoethyl]-5-hydroxy-2(5H)-furanone

A mixture of N-dodecyl-3(2-triethylsilyl-4-furyl)-1-propionamide (92 mg, 0.24 mmol), water (a few drops) and Rose Bengal (5 mg) in acetone (7 ml) was exposed to singlet oxygen at 0° for 3 hours. The residue, after solvent removal, was purified by preparative silica plates to give the titled furanone.

$^1$H NMR (CDCl$_3$): 0.88 (t, 3H, J=6.5 Hz), 1.25 (m, 18H), 1.50 (m, 2H), 2.60 (m, 1H), 2.70 (m, 3H), 3.24 (m, 2H), 5.69 (br, 1H), 5.87 (s, 1H), 6.0 (s, 1H), 6.03 (s, 1H), 6.75 (s, 1H) and 6.79 (s, 1H).

$^{13}$C NMR (CDCl$_3$): 13.8, 22.4, 22.9, 24.6, 26.7, 29.0, 29.1, 29.3, 29.4, 31.7, 33.3, 39.8, 99.9, 118.5, 168.7, 171.5 and 172.0.

HRMS exact mass calculated for C$_{19}$H$_{34}$NO$_4$ (M+H)$^+$ 340.2488, found 340.2466.

EXAMPLE 32

Reacting N-methyl-N-dodecyl-hydrazine with 3-(2-triethylsilyl-4-furyl)-1-propanal gives the corresponding hydrazone. Oxidizing this hydrazone with singlet oxygen gives 4-[3-(N-methyl-N-dodecyl) hydrazinyl]-propyl-5-hydroxy-2(5H)-furanone.

EXAMPLE 33

As in Example 31, but substituting 1-dodecylamine with 1-dodecanol and carry through the reaction sequence to give 4-(2-carbododecyloxy)ethyl-5-hydroxy-2(5)-furanone.

EXAMPLE 34

Reduction of 4-(3-oxo-4-hexadecynyl)-2-triethylsilylfuran with sodium in liquid ammonia gives (E)-4-(3-oxo-4-hexadecenyl)-2-triethylsilylfuran. Oxidizing this intermediate with singlet oxygen gives (E)-4-(3-oxo-4-hexadecenyl)-5-hydroxy-2(5H)-furanone.

EXAMPLE 35

As in Example 31, but substituting 1-dodecylamine with 12-amino-1-dodecanoic acid and carry the reaction sequence through, gives 4-[2-(N-11-carboxyundecyl)amido]-ethyl-5-hydroxy-2(5H)-furanone.

EXAMPLE 36

As in Example 31, but substituting 1-dodecylamine with 12-amino-1-dodecanoic acid and carry the reaction sequence through, gives 4-[2-(12-N, N-dimethylaminododecyl)amido]ethyl-5-hydroxy-2(5H)-furanone.

EXAMPLE 37

The following test procedures may be used to demonstrate activity of the compounds of this invention:

Inhibition of Phospholipase $A_2$

The effect of compounds of this invention on bee venom phospholipase $A_2$ is determined by the following procedure:

a. Bee venom phospholipasae $A_2$ in 10 $\mu$M HEPES (pH 7.4) with 1 mM $CACl_2$ is incubated with vehicle or test agent for 1.0 hour at 41°.

b. 1.36 mM phosphotidylcholine, 2.76 mM Triton X-100 are dispersed in buffer by sonication and then mixed with L-3 phosphatidylcholine, 1-palmitoyl-2-(1-$^{14}$C) palmitoyl for 10 min.

c. Start the reaction by the addition of enzyme (0.495 units/ml).

d. Incubation for 15 sec. at 41° e. Reaction is terminated by addition of 2.5 ml of isopropanol: n-heptane: 0.5M $H_2SO_4$ (40:10:1; v:v:v).

f. 2.0 ml n-heptane and 1.0 ml $H_2O$ added; mixture centrifuged.

g. 2.0 ml n-heptane removed and treated with 200-300 mg of silica gel HR60.

h. Samples centrifuged; 1 ml of n-heptane SN removed and added to 10 ml scintillation fluid.

i. Samples counted on a scintillation counter.

Inhibition of Phoshoinositide-specific Phospholipase C

The effect of compounds of this invention on phosphoinositide-specific phospholipase C may be determined by procedures described by Bennett et al, Molecular Pharmacology 32:587-593 (1987). Mouse Ear Anti-Inflammatory Assay Test compound and phorbol myristate acetate (PMA) are topically applied simultaneously to the pinnae of the left ears of mice. PMA alone is applied to the right ear. Three hours add 20 minutes after application, the mice are sacrificed, left and right ears removed, and standard sized bores taken. Edema (inflammation) is measured as the difference in weight between left and right ears [Van Arman, C. G; Clin. Pharmacol. Ther. (1974) 16:900-904].

Inhibition of Ornithine Decarboxylase (ODC)

Tape-stripping mouse epidermis and TPA are quick and convenient methods of inducing ODC activity. M. Connor and N. Lowe (Cancer Res. 43, 5174, 1983; Brit. J. Dermatol. 275, 98, 1984) have studied the ability of retinoids to inhibit ODC. Trans-retinoic acid, 13-cis retinoic acid, and etretinate were all active at inhibiting ODC and therapeutically active in humans. Therefore, inhibition of ODC is an in vivo method to demonstrate the potential efficacy of drugs for epidermal hyperproliferation such as psoriasis. Lowe et al (J. Amer. Acad. Dermatol. 6:697, 1982) have shown that polyamines and ODC are elevated in psoriasis.

In vitro methods have also been useful in determining the anti-hyperproliferative activity of drugs. C. Marcelo and J. Tomich (J. Invest. Dermatol. 81, 64s, 1983) have shown that neonatal mouse keratinocyte cultures can be used to identify drugs that inhibit DNA synthesis. More recently, R. Weiss, Eichner, R. and Sunn, T. T., J. Cell Biol; 98:1397-1406, (1984) have shown that epidermal cultures are in fact a model of epidermal hyperproliferation and therefore a good model for testing drugs that inhibit hyperproliferation. Calcium Channel (mobilization) Inhibition Assay.

Polymorphonuclear leukocytes (PMNa), gastric glands, $GH_3$ cells, A431 cells, spleen cells, human keratinocyte corneal cells, etc., were loaded with the $Ca^{2+}$ sensitive fluorescent dye, Fura-2. The appropriate cell type was chosen and the potency and efficacy of the anti-inflammatory furanones on calcium mobilization, calcium channel inhibition quantitated. The methods used for A431 cells listed below are representative of those used for other cells.

A431 cells were detached using a 5-10 min trypsin-EDTA treatment whereas $GH_3$ cells were treated 2 to 5 min with a 1% pancreatin solution. Cells were immediately washed twice in a 20 mM HEPES buffer (pH 7.4) containing 120 mM NaCl, 6 mM KCl, 1 mM $MGSO_4$, 1 mg/ml glucose and 1 mg/ml pyruvate and 1.4 mM calcium (medium A). Approximately $5 \times 10^6$ cells were suspended in medium A and incubated with 4$\mu$ fura-2-AM for 15 min at 37° C. After washing the fura-2 loaded cells, the uptake of dye was checked using fluorescence microscopy and found to be evenly distributed in the cytosol of all cells. Fluorescence was continuously recorded with a Perkin-Elmer LS-5 spectrofluorometer. The excitation wavelength was set at 500 nm. The cell suspension was continually stirred, maintained at 37° C. and equilibrated for approximately 5 min before addition of various agents. $[Ca^{2+}]_i$ was calculated using the following formula:

$$[Ca^{2+}]_i = 220 \frac{F - F_{min}}{F_{max} - F}$$

All fluorescence values were measured relative to a EGTA-quenched signal determined as follows: f was the relative fluorescence measurement of the sample. $F_{max}$ was determined by lysing the cells with digitonin (100 μg/ml) in DMSO. After $F_{max}$ was determined the pH was adjusted to 8, with NaOH and $Ca^{2+}$ chelated with 3 mM EGTA to totally quench the fura-w signal and obtain $F_{min}$.

When quin-2 was used, cells were incubated with 10 μm quin.2 at 37° C. for 1 hr, washed and then used.

What is claimed is:

1. A compound of the formula:

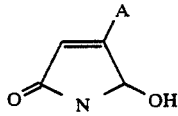

in which
A is

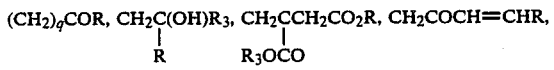

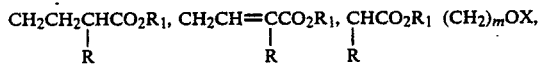

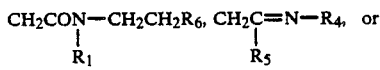

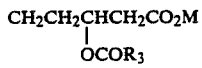

n is 1 or 2;
q is 1-4;
m is 8-12;
R is $C_7$-$C_{14}$ alkyl, $C_7$-$C_{14}$ alkoxide, $NR_3(CH_2)_pZ$ or C≡CM;
p is 2-8;
Z is H, $N(R_3)_2$ or $CO_2H$;
$R_1$ is hydrogen or $C_1$-$C_4$ alkyl;
$R_2$ is $C_7$-$C_{14}$ alkyl or phenyl;
M is $C_7$-$C_{14}$ alkyl; phenyl($C_1$-$C_4$ alkyl) optionally substituted on the phenyl ring by 1-3 halo substituents; pyridyl($C_1$-$C_4$ alkyl) or naphthyl($C_1$-$C_6$ alkyl);
$R_4$ is O—($C_8$-$C_{14}$ alkyl) or NH($C_8$-$C_{14}$ alkyl); and $R_5$ is hydrogen or $R_4$ is OH and $R_5$ is o-hydroxyphenyl;
X is hydrogen, acetyl, $PO(OH)_2$ or $CO(CH_2)_3N(R_{32})$·HCl;
$R_3$ is $C_1$-$C_4$ alkyl and
$R_6$ is phenyl or $C_4$-$C_{12}$ alkyl.

2. A compound of claim 1 in which A is $CH_2CO_2M$, $CH_2CH_2OCOR$, $(CH_2)_nCH=CHCOR$, $(CH_2)_qCOR$,

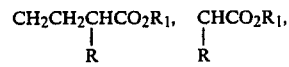

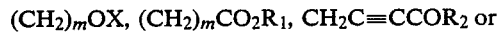

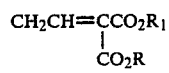

3. A compound of claim 1 in which A is $CH_2CO_2M$, $CH_2CH_2OCOR$, $(CH_2)_nCH=CHCOR$ or

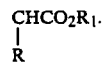

4. A compound of claim 3 in which A is $CH_2CH=CHCOR$.

5. The compound which is 4-(5-oxo-3-hexadecenyl)-5-hydroxy-2(5H)-furanone.

6. The compound which is 4-(3-dodecanoyloxypropyl)-5-hydroxy-2(5H)-furanone.

7. The compound which is 4-(2-carbomethoxytridecyl)-5-hydroxy-2(5H)-furanone.

8. The compound which is 4-(2-carbooctanoxy)ethyl-5-hydroxy-2(5H)-furanone.

9. A anti-flammatory pharmaceutical composition which comprises a pharmaceutical carrier and a therapeutically effective amount of a compound of claim 1.

10. A method of treating inflammation or an allergic response in a mammal which comprises administering to a mammal a therapeutically effective amount of a compound of claim 1 alone or in conjunction with a pharmaceutically acceptable excipient.

11. A method of treating psoriasis which comprises administering to a mammal a therapeutically effective amount of a compound of claim 1 either alone or in conjunction with a pharmaceutically acceptable excipient.

* * * * *

UNITED STATES PATENT AND TRADEMARK OFFICE
CERTIFICATE OF CORRECTION

PATENT NO. : 5,059,611
DATED : October 22, 1991
INVENTOR(S) : Gary C. M. Lee

It is certified that error appears in the above-identified patent and that said Letters Patent is hereby corrected as shown below:

Column 2, line 33, "$C_7$-C" should be --$C_7C_{14}$--;

Column 2, line 38, "$C_7$-C" should be --$C_7C_{14}$--;

Column 7, line 24, "(brin)," should be --(brine),--;

Column 8, line 51, after "Hz)." start a new paragraph;

Column 12, line 27, "6H)," should be --6H);--;

Column 14, line 10, "2H." should be --2H,--;

Column 14, line 33, "71.1" should be --171.1--;

Column 15, line 4, "121.0." should be --121.0,--;

Column 15, line 33, ..."OSI"... should be ...--OSi--...;

Column 22, line 56, ..."oxotridecylohosphonate" should be ...--oxotridecylphosphonate--;

Column 24, line 58, after "0.75" insert --(-- before the "q,"; and

Column 28, line 6, "add" should be --and--.

Signed and Sealed this

Twenty-third Day of November, 1993

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,059,611

DATED : October 22, 1991

INVENTOR(S) : Gary C. M. Lee

It is certified that error appears in the above-identified patent and that said Letters Patent is hereby corrected as shown below:

Column 9, line 10, "methyl3-("... should be --methyl 3-(--...;

Column 14, line 10, after "7.5" insert --Hz-- before the ")";

Column 20, line 45, "ropionate" should be --propionate--;

Column 20, line 66, after "mg" delete the --)--;

Column 22, line 20, after "(CDCl$_3$)" insert --:--;

Column 22, line 24, after "abundance)" insert --:--;

Column 22, line 33, "intetrahydrofuran" should be --in tetrahydrofuran--;

Column 25, line 12, "18.73" should be --187.3--;

Column 27, line 14, "2(5)-furanone." should be --2(5H)-furanone--; and

Column 27, line 44, "phospholipasae" should be --phospholipase--.

Signed and Sealed this

Fourth Day of January, 1994

Attest:

BRUCE LEHMAN

*Attesting Officer*   Commissioner of Patents and Trademarks